(12) United States Patent
Agarwal et al.

(10) Patent No.: US 9,956,008 B2
(45) Date of Patent: May 1, 2018

(54) STABILIZED SPINAL FIXATION DEVICE

(71) Applicant: The University of Toledo, Toledo, OH (US)

(72) Inventors: Anand K. Agarwal, Toledo, OH (US); Vijay K. Goel, Toledo, OH (US); John R. D'Onofrio, Toledo, OH (US); Nathaniel E. DuBois, Toledo, OH (US); Jared R. Pack, Toledo, OH (US); David J. Taylor, Toledo, OH (US)

(73) Assignee: The University of Toledo, Toledo, OH (US)

( * ) Notice: Subject to any disclaimer, the term of this patent is extended or adjusted under 35 U.S.C. 154(b) by 98 days.

(21) Appl. No.: 14/784,855

(22) PCT Filed: Apr. 25, 2014

(86) PCT No.: PCT/US2014/035464
§ 371 (c)(1),
(2) Date: Oct. 15, 2015

(87) PCT Pub. No.: WO2014/176507
PCT Pub. Date: Oct. 30, 2014

(65) Prior Publication Data
US 2016/0058478 A1 Mar. 3, 2016

Related U.S. Application Data

(60) Provisional application No. 61/815,992, filed on Apr. 25, 2013.

(51) Int. Cl.
A61B 17/70 (2006.01)
A61B 17/00 (2006.01)

(52) U.S. Cl.
CPC ...... *A61B 17/7049* (2013.01); *A61B 17/7032* (2013.01); *A61B 17/7035* (2013.01); *A61B 17/7056* (2013.01); *A61B 2017/00867* (2013.01)

(58) Field of Classification Search
CPC ............ A61B 17/7032; A61B 17/7035; A61B 17/7049; A61B 17/7056; A61B 17/707;
(Continued)

(56) References Cited

U.S. PATENT DOCUMENTS 5,374,267 A * 12/1994 Siegal ................ A61B 17/7056
606/250
5,476,464 A * 12/1995 Metz-Stavenhagen A61B 17/7037
606/266

(Continued)

FOREIGN PATENT DOCUMENTS

CN 2400067 Y 10/2000
CN 1305783 A 8/2001

OTHER PUBLICATIONS

CN Office Action, Application No. 201480030935.2, dated May 22, 2017.
(Continued)

*Primary Examiner* — Jan Christopher Merene
*Assistant Examiner* — Atiya Mahmud
(74) *Attorney, Agent, or Firm* — MacMillian, Sobanski & Todd, LLC

(57) ABSTRACT

A spinal fixation device includes a device body configured for implantation in a human body and a clamp that is formed from shape memory material and attached to the device body.

20 Claims, 38 Drawing Sheets

(58) Field of Classification Search
CPC ............ A61B 17/7065; A61B 17/8685; A61B 2017/0043; A61B 2017/8655
See application file for complete search history.

(56) References Cited

U.S. PATENT DOCUMENTS

| | | | | |
|---|---|---|---|---|
| 5,540,689 | A * | 7/1996 | Sanders | A61B 17/7032 24/531 |
| 5,586,983 | A * | 12/1996 | Sanders | A61B 17/7002 24/457 |
| 5,688,273 | A * | 11/1997 | Errico | A61B 17/7037 606/276 |
| 6,911,030 | B1 | 6/2005 | Vanacker et al. | |
| 7,883,532 | B2 * | 2/2011 | Biscup | A61B 17/7047 606/246 |
| 8,043,337 | B2 * | 10/2011 | Klyce | A61B 17/7047 606/252 |
| 2007/0093832 | A1 * | 4/2007 | Abdelgany | A61B 17/7037 606/250 |
| 2007/0161990 | A1 | 7/2007 | Hillyard et al. | |
| 2007/0213723 | A1 * | 9/2007 | Markworth | A61B 17/7049 606/914 |
| 2008/0065074 | A1 | 3/2008 | Yeung et al. | |
| 2011/0144694 | A1 | 6/2011 | Laeng et al. | |
| 2011/0184463 | A1 * | 7/2011 | Schwend | A61B 17/705 606/258 |
| 2011/0245876 | A1 * | 10/2011 | Brumfield | A61B 17/7035 606/264 |

OTHER PUBLICATIONS

European Search Report, Application No. EP14788930, dated Aug. 17, 2016.

* cited by examiner

STABILIZED SPINAL FIXATION DEVICE

CROSS-REFERENCE TO RELATED APPLICATIONS

This application claims the benefit of U.S. Provisional Application No. 61/815,992, filed Apr. 25, 2013, the disclosure of which is incorporated herein by reference.

STATEMENT REGARDING FEDERALLY SPONSORED RESEARCH

This invention was not made with any government support, and the government has no rights in this invention.

BACKGROUND OF THE INVENTION

Various embodiments of a spinal fixation device are described herein. In particular, the embodiments described herein relate to an improved spinal fixation device used to stabilize and fuse the human spine.

Devices and methods for correcting spinal deformities are known and use implants anchored to portions of the posterior spine at various locations on the vertebrae, such as on the lamina, transverse process, or pedicle, as shown in FIG. 26. Such known devices stabilize the spine by fusing the spinal column into a single rigid construct, and typically include pedicle screws or hooks that are anchored to the spine and connected by fusion rods.

The placement of pedicle screws requires a large amount of time and great effort by a surgeon, and placement location options are limited. A surgeon must first very exactly position and form a screw hole in the pedicle bone. The hole must be tapped and then the pedicel screw must be screwed into the tapped hole in the pedicle bone.

Known spinal hooks may be placed at various locations of the vertebrae, including on the lamina, transverse process, and pedicle. The design of known spinal hooks requires the surgeon to place two hooks in an opposing relationship, and then tighten each hook to the fusion rod to hold the hooks to the vertebrae. The size and shape of the portion of the spinal hook that engages the vertebrae does not perfectly mate or engage with the portion of a vertebra to which it will be attached. Further, known spinal hooks have no stabilization mechanism and are therefore not held to the vertebrae until a fusion rod is attached between two or more spinal hooks. Known spinal hooks can therefore be unstable during surgery prior to and during attachment of the fusion rod, and may fall off the bone during surgery prior to the fusion rod being attached, causing difficulty for the surgeon. Accordingly, there is a need for more stable and reliable spinal hooks.

SUMMARY OF THE INVENTION

The present application describes various embodiments of a spinal fixation device. One embodiment of the spinal fixation device includes a device body configured for implantation in a human body and a clamp formed from shape memory material and attached to the device body.

In an additional embodiment, the clamp is movable between an open position and a closed position.

In another embodiment, when in the open position the clamp is configured to be positioned one of against and at least partially around a portion of a vertebra, and when in the closed position the clamp exerts a clamping force on the portion of the vertebra, thereby attaching the spinal fixation device to the vertebra.

In another embodiment, the clamp responds to changes in temperature such that at a first temperature, the clamp is in an open position, and at a second temperature, higher than the first temperature, the clamp is in a closed position.

In another embodiment, the first temperature is room temperature or about 21 degrees C., and the second temperature is human body temperature or about 37 degrees C.

In another embodiment, the clamp is substantially U-shaped.

In additional embodiments, the clamp may be configured as an elongated member having a bone engaging surface, may have an arcuate shape, may be mounted to the device body in a cantilevered manner, or may be V-shaped or U-shaped and configured to exert a clamping force on a portion of a vertebra positioned between the clamp and the shoe portion.

In another embodiment, the clamp is formed in a closed position and configured to be positioned one of against and at least partially around a portion of a vertebra.

In another embodiment, the clamp formed in a closed position responds to changes in temperature such that when the clamp is deformed or enlarged when positioned against or least partially around a portion of a vertebra, upon reaching human body temperature or about 37 degrees, the clamp will attempt to return to its closed shape, thereby exerting a clamping force on the portion of the vertebra.

In another embodiment, the device body includes a base and an arcuate shoe portion.

In another embodiment, the shoe portion is formed from shape memory material.

In another embodiment, the shoe portion includes a bone engaging surface having at least one tooth extending radially outward of the bone engaging surface, the at least one tooth configured to engage and anchor the shoe portion in place relative to a portion of a vertebra positioned within the shoe portion.

In another embodiment, the base and the shoe portion are connected by a joint that allows poly-axial movement between the base and the shoe portion, such as a ball joint.

In another embodiment, the base includes a longitudinally extending pin bore centrally formed through base, and a locking pin, wherein upon insertion of the locking pin into the pin bore, the locking pin urges an outside surface of the base to frictionally engage an inside surface of the shoe portion, preventing movement of the base relative to the shoe portion.

In another embodiment, the base and the shoe portion are connected by a joint that allows translational movement between the base and the shoe portion.

In another embodiment, the spinal fixation device further includes a set screw extending between the base and the shoe portion, the set screw configured to urge a portion of a vertebra against a bone engaging surface of the shoe portion, thereby exerting a clamping force on the portion of the vertebra.

In another embodiment, the clamp is attached to the device body by a fastener, such as a rivet, a threaded fastener, or a fastener configured to be press fit to the device body.

In another embodiment, the clamp is integrally formed with the device body.

Other advantages of the spinal fixation device will become apparent to those skilled in the art from the following detailed description, when read in view of the accompanying drawings.

DETAILED DESCRIPTION OF THE PREFERRED EMBODIMENTS

Figure 1:
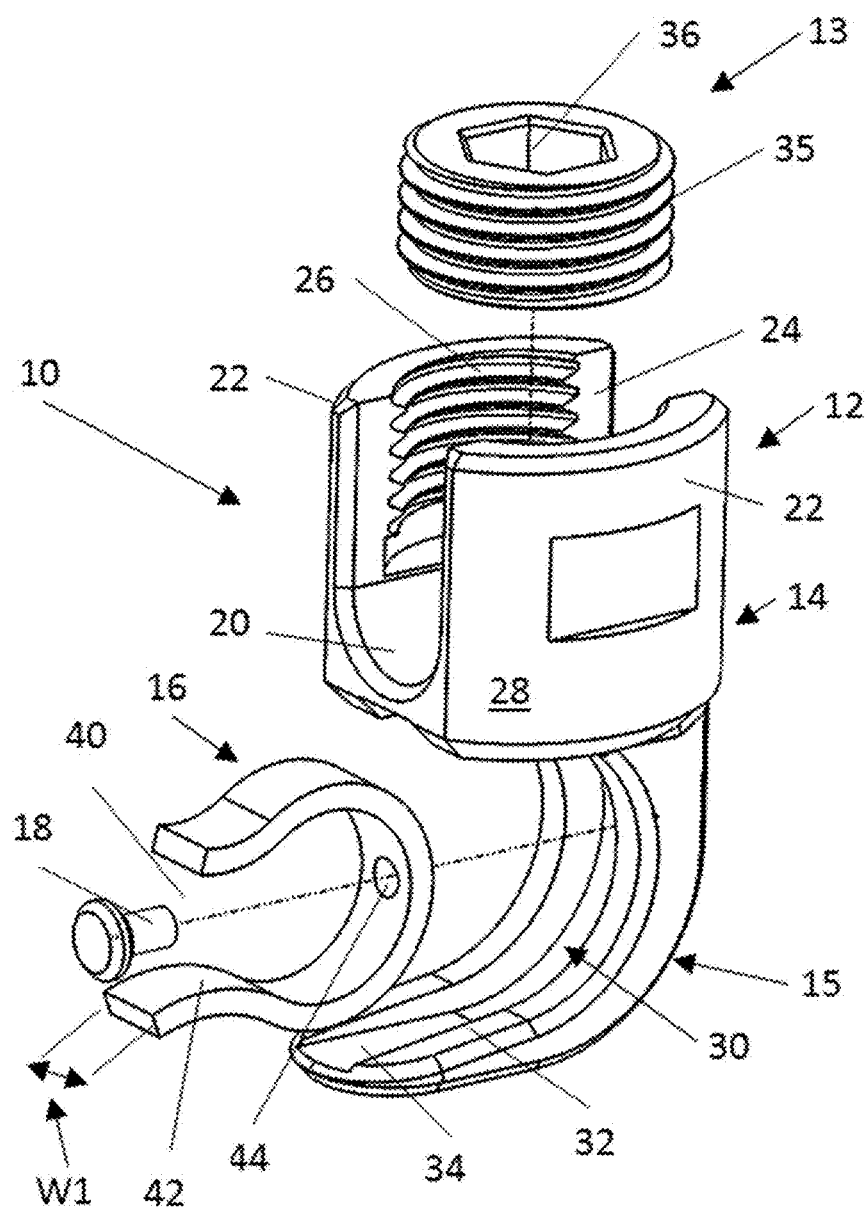
FIG. 1 is an exploded perspective view of a first embodiment of a spinal fixation device in accordance with this invention.

The embodiments of the invention disclosed below generally provide improvements to various types of spinal fixation devices used to stabilize and fuse the human spine.

Referring to the drawings, particularly to FIGS. 1 through 5, a first embodiment of a spinal fixation device 10 is shown. The illustrated spinal fixation device 10 includes a hook base 12, a set screw 13, a spring or clamp 16, and a fastener 18, each of which will be described in detail below. The spinal fixation device 10 is configured for attachment to a fusion rod 19, shown in FIG. 2.

The hook base 12 includes a first or upper portion 14 and a hook or shoe portion 15. The upper portion 14 includes a channel 20 configured to receive the fusion rod 19, and two outwardly extending side walls 22. Interior surfaces 24 of the side walls 22 include threads 26. In the illustrated embodiment, outside surfaces 28 of the side walls 22 are arcuate, however the outside surfaces 28 may have any other desired shape.

Figure 3:
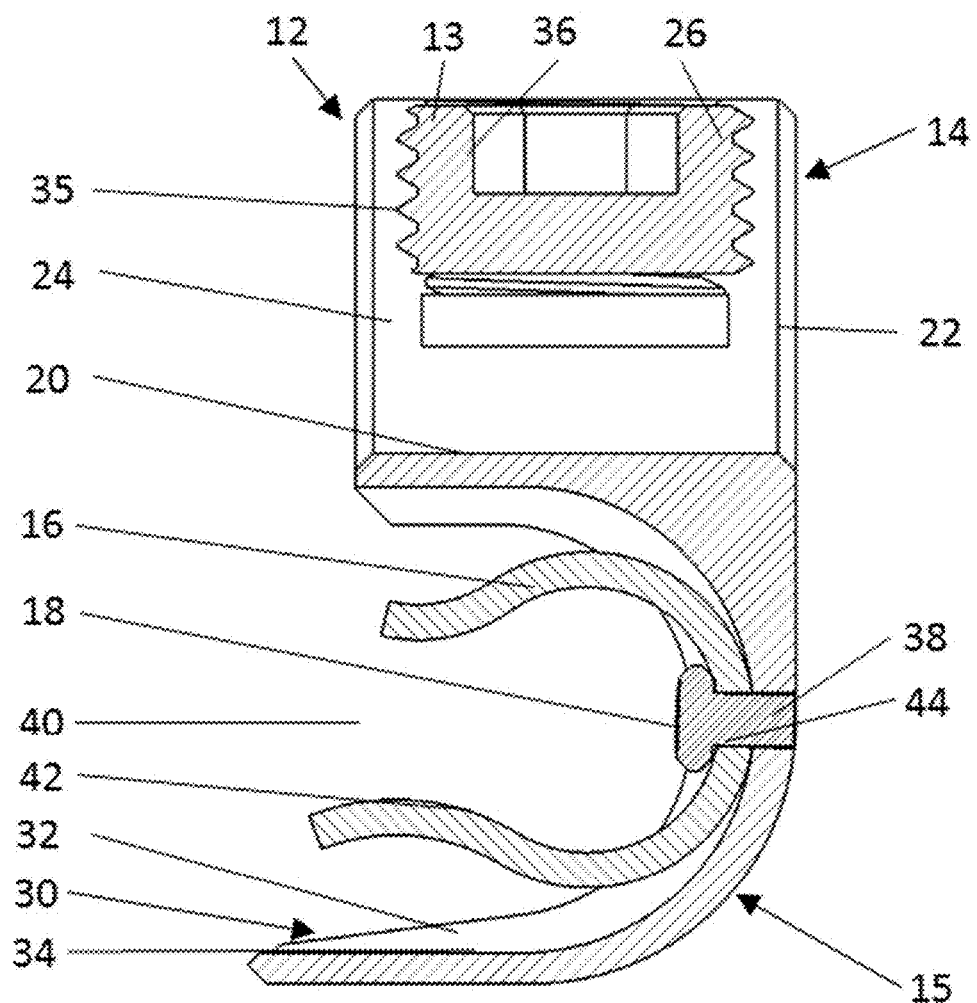
FIG. 3 is a cross sectional view of the first embodiment of the spinal fixation device illustrated in FIG. 2.
Figure 5:
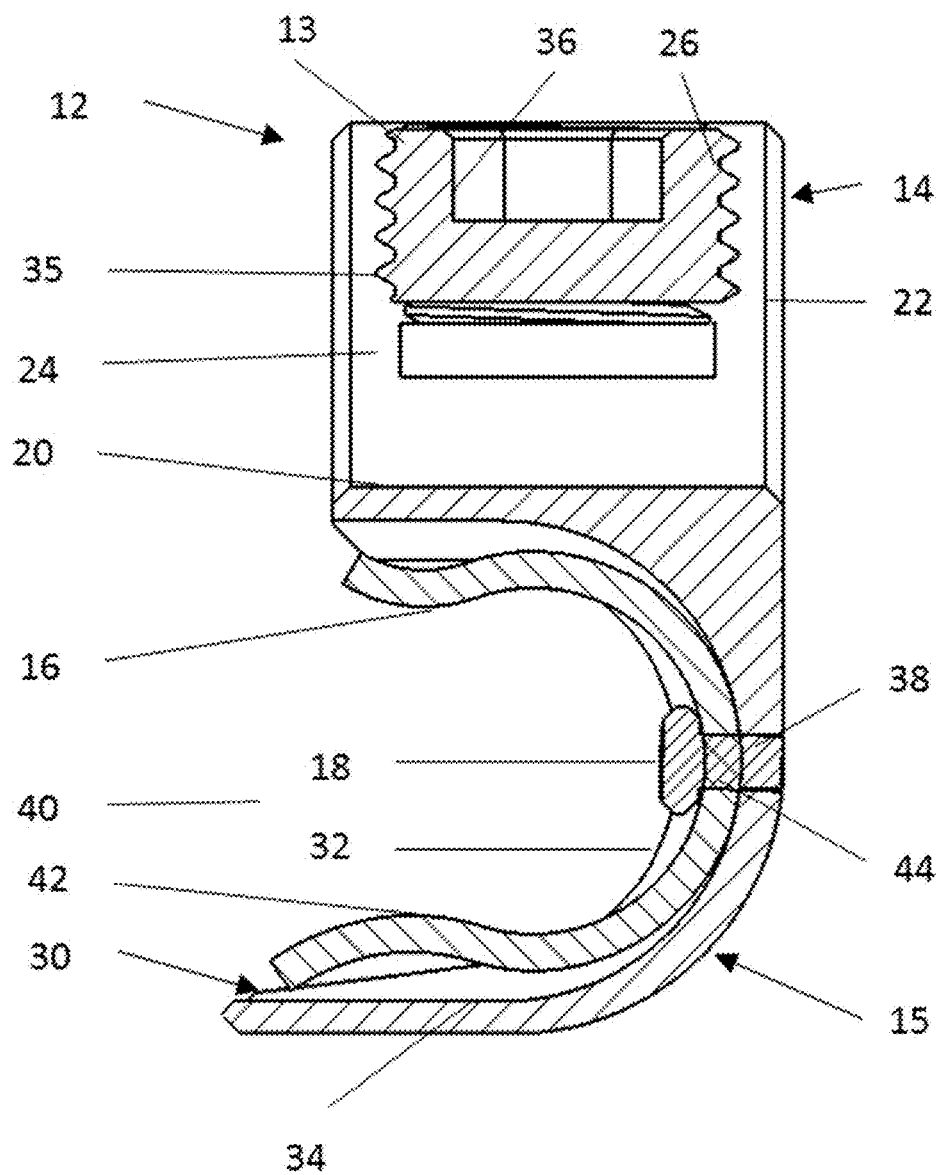
FIG. 5 is a cross sectional view of the first embodiment of the spinal fixation device illustrated in FIG. 4.

The shoe portion 15 extends outwardly from the upper portion 14 opposite the side walls 22 and includes a bone facing surface 30. In the illustrated embodiment, the shoe portion 15 has an arcuate shape configured for attachment to various locations on the vertebrae, such as on the lamina, transverse process, or pedicle. As best shown in FIGS. 3 and 5, a fastener receiving aperture 38 is formed in the shoe portion 15. The illustrated bone facing surface 30 also includes longitudinally extending ribs 32 defining a groove 34. Alternatively, the bone facing surface 30 may have any desired number of ribs 32 or may be formed without ribs, such as shown in the embodiments illustrated in FIGS. 6 through 25. The shoe portion 15 and its bone facing surface 30 may be formed in any desired shape so as to engage and facilitate attachment to various locations on the vertebrae. The exemplary set screw 13 includes external threads 35 and a tool-receiving aperture 36.

The clamp 16 is substantially U-shaped defining a clamp opening 40 and having a bone engaging surface 42. A fastener receiving aperture 44 is formed in the clamp 16. The clamp 16 has a width W1 and is configured to nest within the groove 34 of the bone facing surface 30. Alternatively, the clamp 16 may have any desired width W1, including a width smaller than the groove 34 and a width slightly larger than the width of the shoe portion 15.

In the illustrated embodiment, the clamp 16 is formed from shape memory material. As described below in detail, the shape memory material assists in stabilizing the shoe portion 15 of the hook base 12 by gripping the vertebrae. As used herein, shape memory material is a material that may be formed in a first shape, subsequently deformed, and will return to its pre-deformed first shape when heated. In the exemplary embodiment illustrated, the shape memory material is nickel-titanium alloy, also known as nitinol. Alternatively, other alloys and polymers having shape memory properties may be used. One example of such a polymer is Norsorex®, manufactured by Astrotech Advanced Elastomerproducts GmbH.

The fastener 18 may be any desired type of fastener suitable for attaching the clamp 16 to the shoe portion 15. Non-exclusive examples of suitable fasteners include threaded fasteners, rivets, and attachment by welding. Additionally, the clamp 16 may be integrally formed with the shoe portion 15.

The hook base 12, set screw 13, and fastener 18 may be formed from any desired material. Non-exclusive examples of suitable material include titanium and stainless steel.

Figure 2:
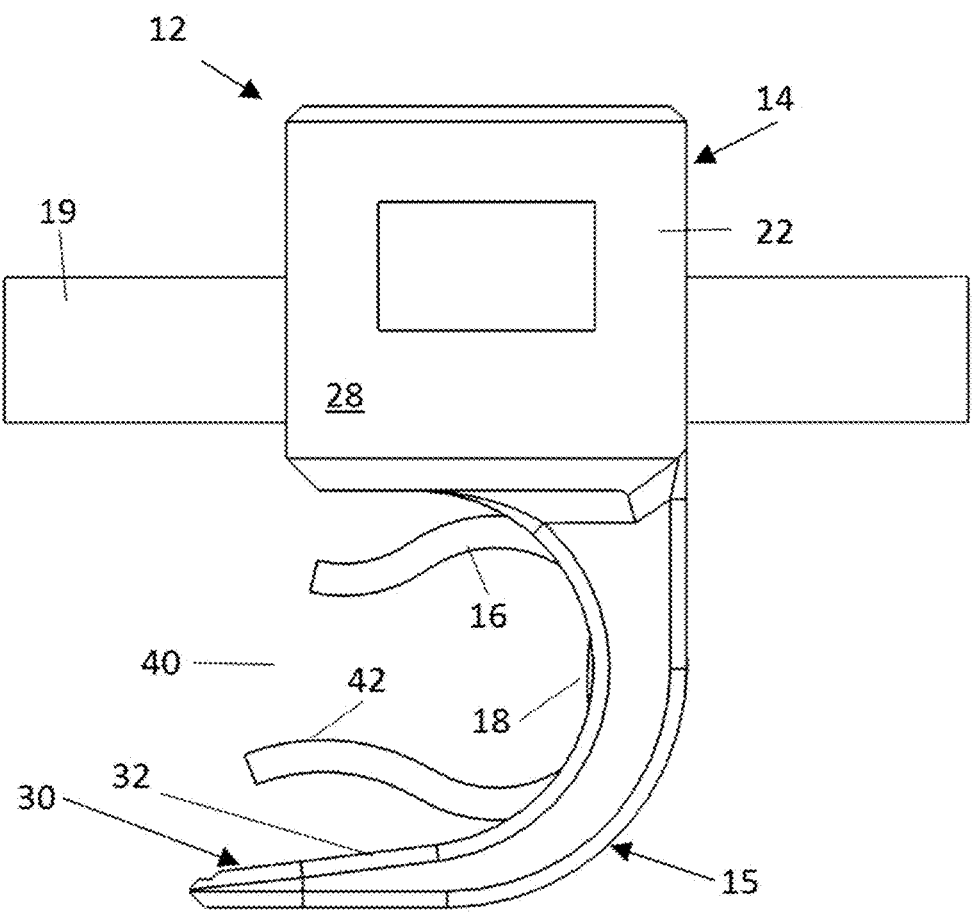
FIG. 2 is a side elevational view of the first embodiment of the spinal fixation device illustrated in FIG. 1, wherein the clamp is shown in a closed position.
Figure 4:
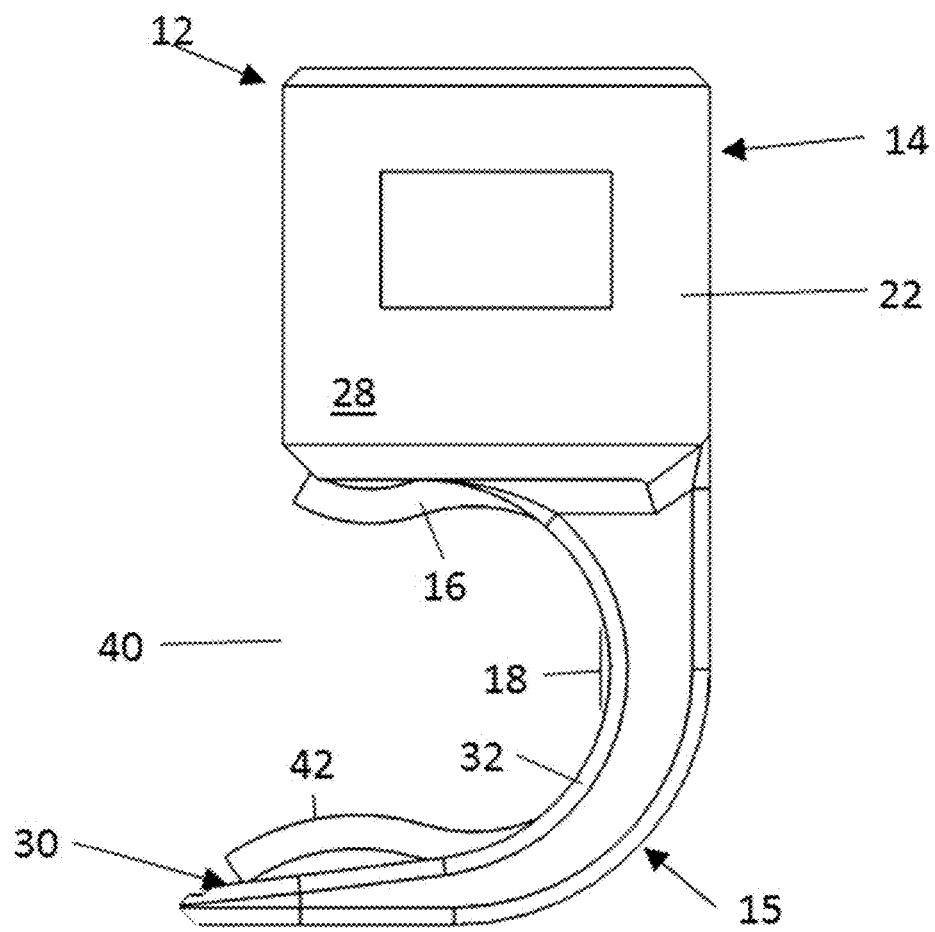
FIG. 4 is a side elevational view of the first embodiment of the spinal fixation device illustrated in FIG. 1, wherein the clamp is shown in an open position.

Referring now to FIGS. 2 through 5 and 26, the clamp 16 may move between an open position as shown in FIGS. 4 and 5, and a closed position as shown in FIGS. 2 and 3.

In a first embodiment of the clamp 16, the shape memory material changes shape with a change in temperature, such as the change that occurs between room temperature and the temperature of a patient's body. For example, when the clamp 16 is exposed to a temperature at or about room temperature, i.e., at or about 21 degrees C., the shape memory material clamp 16 will be in the open position. In the open position, a surgeon can more easily position and implant the spinal fixation device 10 on a desired portion of a vertebra. After being implanted in the patient, the shape memory material clamp 16 will enter a temperature transitional stage as the temperature of the shape memory material clamp 16 rises to the temperature of the patient's body, i.e., at or about 37 degrees C. During this transitional stage, the opening 40 of the shape memory material clamp 16 becomes smaller as it moves from the open position to the closed position. Upon reaching a temperature of about 37 degrees C., the shape memory material clamp 16 will have moved to the closed position, as shown in FIGS. 2 and 3. In the closed position, the clamp 16 exerts a capturing or clamping force on the portion of the vertebra to which it is attached.

In a second embodiment of the clamp 16, the shape memory material clamp 16 will be pre-configured in a desired engaged or closed position prior to and during surgical implantation. In this embodiment, the shape memory material clamp 16 will be in the closed position upon implantation. As the shape memory material hook 16 is implanted, the vertebra to which the shape memory material clamp 16 is attached will cause the opening 40 of the shape memory material clamp 16 to expand to the thickness of the vertebra. After implantation, the shape memory material of the clamp 16 will attempt to return to its original shape, i.e., the closed position, thereby exerting a capturing force on the portion of the vertebra to which it is attached. It will be understood that in both the first and second embodiments of the clamp 16, the clamp 16 may have any desired shape corresponding to the size and shape of the portion of the vertebra to which it will be attached, or to otherwise properly fit in the patient's body.

Once a desired number of spinal fixation devices 10 have been positioned on the vertebrae, the fusion rod 19 may be positioned in the channel 20 of each spinal fixation device 10. The fusion rod 19 may then be attached to each spinal fixation device 10 by tightening the set screw 13 of each spinal fixation device 10.

Advantageously, the clamp 16 of the spinal fixation device 10 allows the spinal fixation device 10 to remain stable after being positioned on a vertebra, and during attachment of the fusion rod 19. The spinal fixation device 10 needs only to be placed at a desired location on a vertebra. The shape memory material clamp 16 exerts a clamping force on the vertebra to which it is attached, thus preventing the spinal fixation device 10 from falling off the vertebra during implantation of the spinal fixation device 10 and subsequent attachment of the fusion rod 19.

Additionally, it will be understood that the shoe portion 15 of the hook base 12, and any of the embodiments of the shoe portion illustrated in FIGS. 6 through 25, may be formed from shape memory material as described above. A shoe portion 15 formed from shape memory material may have any desired shape corresponding to the size and shape of the portion of the vertebra to which it will be attached, or to otherwise properly fit in the patient's body. A hook base 12 having a shoe portion 15 formed from shape memory material may be provided with or without the shape memory material clamp 16.

Figure 6:
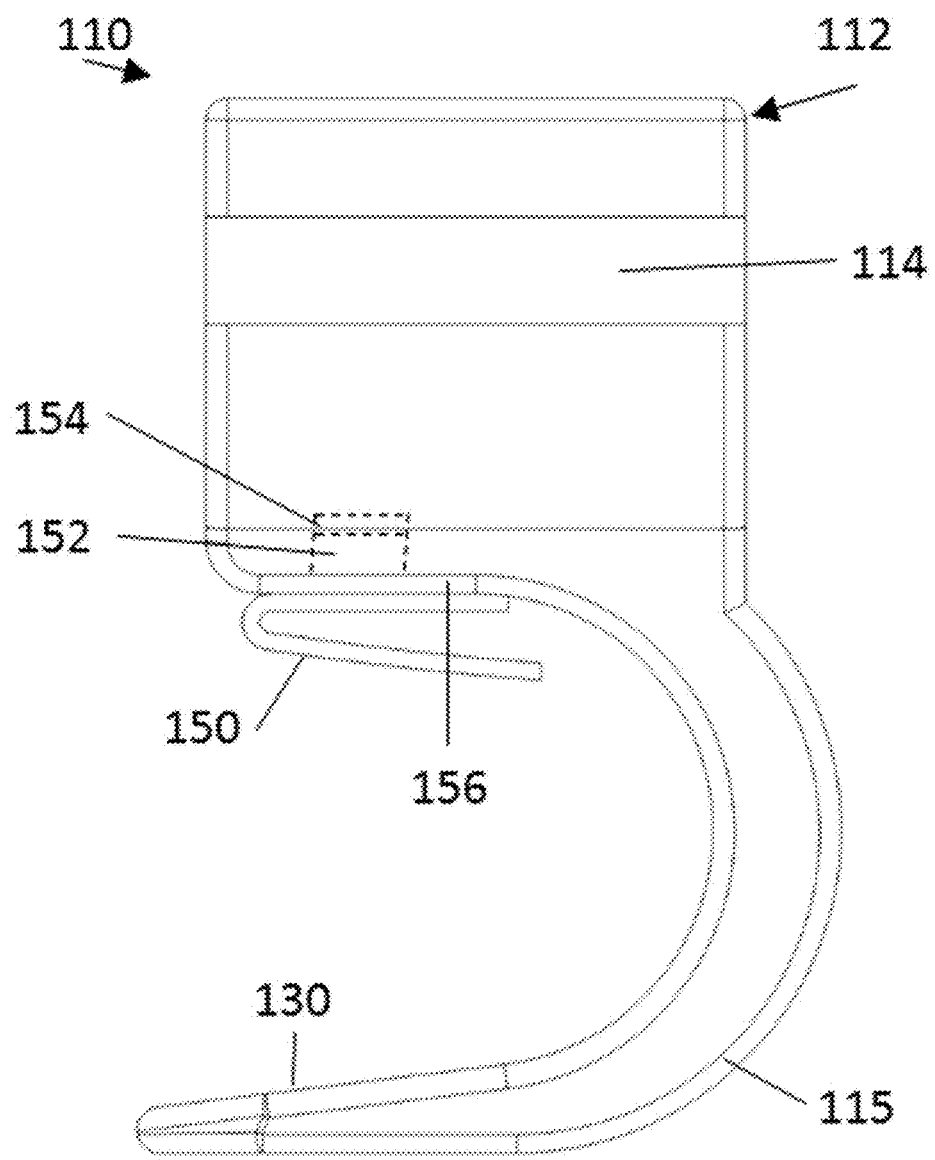
FIG. 6 is a side elevational view of a second embodiment of a spinal fixation device in accordance with this invention.
Figure 7:
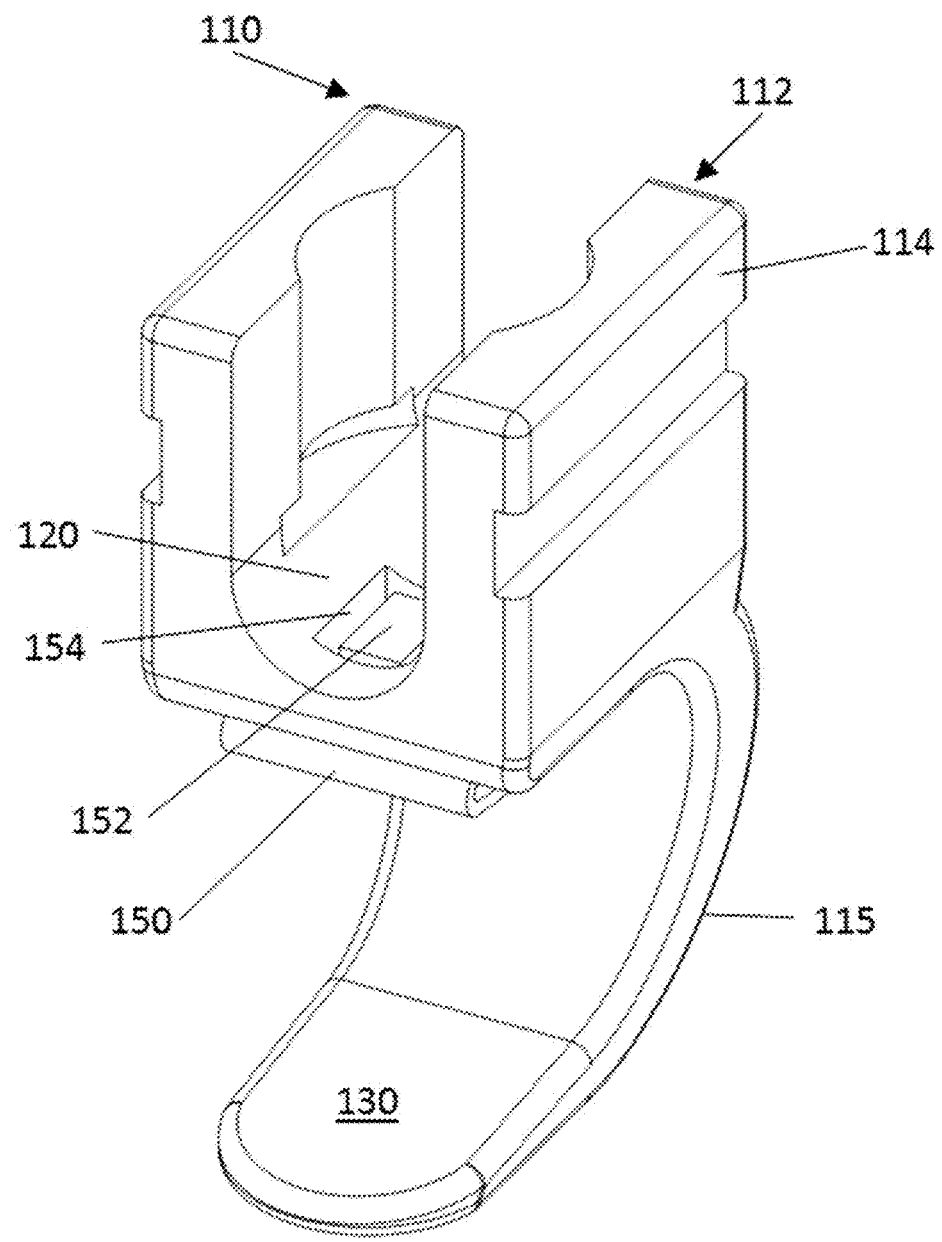
FIG. 7 is a perspective view of the second embodiment of the spinal fixation device illustrated in FIG. 6.

A second embodiment of a spinal fixation device is shown at 110 in FIGS. 6 and 7. The illustrated spinal fixation device 110 is similar to the spinal fixation device 10 and includes a hook base 112 having an upper portion 114 and a shoe portion 115. The upper portion 114 includes a channel 120 and an aperture 154 formed in a shoe-facing surface 156 thereof. The illustrated shoe portion 115 includes a bone facing surface 130. If desired, the bone facing surface 130 may include ribs, such as the ribs 32 shown in FIGS. 1 through 5. The spinal fixation device 110 also includes spring member 150. The spring member 150 is substantially V-shaped and includes a mounting stud 152.

In the illustrated embodiment, the mounting stud 152 is press-fit into the aperture 154. Alternatively, the spring member 150 may be attached to the spinal fixation device 110 by any desired means, such as with a threaded fastener, a rivet, or by welding.

In the illustrated embodiment, the spring member 150 is formed from shape memory material as described above. Alternatively, the spring member 150 may be formed from metal, such as stainless steel, or spring steel.

The spring member 150 is configured and positioned to exert a clamping force on a vertebra to which the shoe portion 115 is attached, thus preventing the spinal fixation device 110 from falling off the vertebra during implantation of the spinal fixation device 110 and subsequent attachment of the fusion rod 19. The spring member 150 may have any desired shape configured to exert a clamping force on a vertebra to which the shoe portion 115 will be attached.

As described above regarding a second embodiment of the clamp 16, the spring member 150 will be pre-configured in a final engaged, closed or clamped shape and position, as shown in FIGS. 6 and 7, such that the spring member 150 will be in the engaged, closed or clamped position upon implantation. As the spinal fixation device 110 is implanted, the vertebra to which it is attached will engage the spring member 150 and urge the spring member 150 toward the upper portion 114. After implantation, the shape memory material spring member 150 will attempt to return to its original shape and position, i.e., the engaged, closed or clamped shape and position shown in FIGS. 6 and 7, thereby exerting a clamping force on the portion of the vertebra to which the spinal fixation device 110 is attached.

Figure 8:
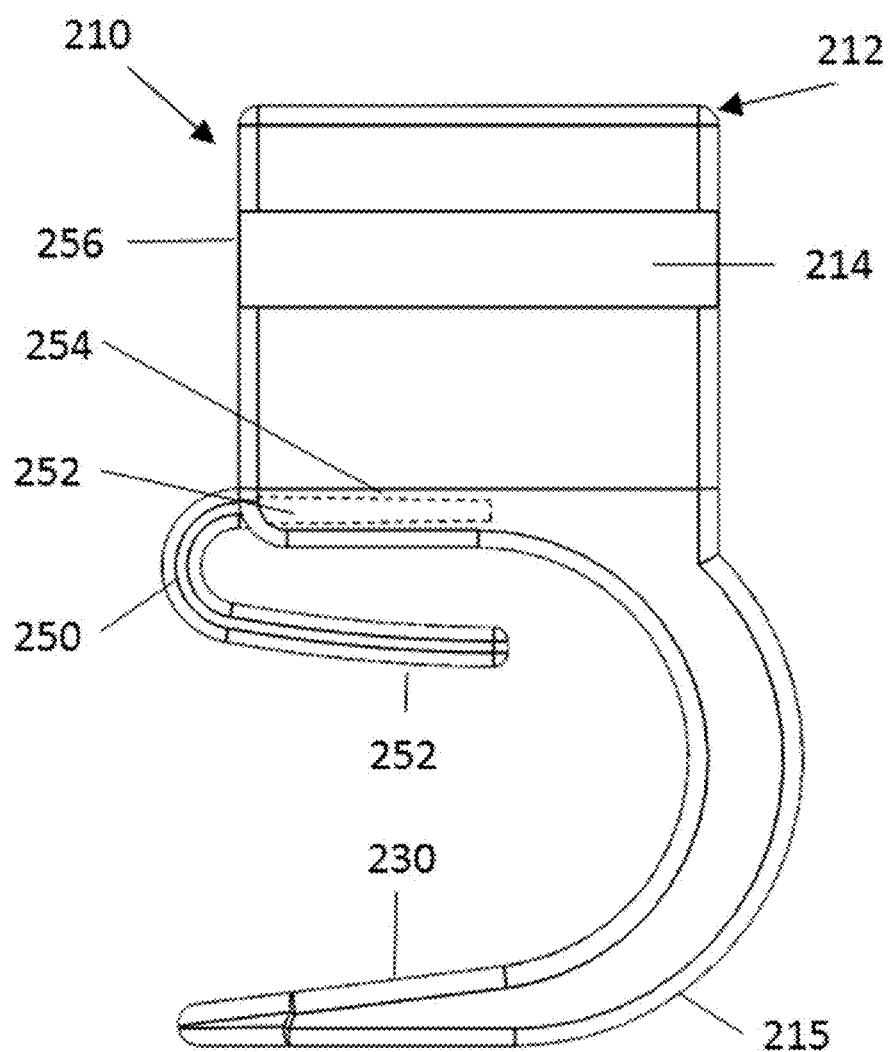
FIG. 8 is a side elevational view of a third embodiment of a spinal fixation device in accordance with this invention.
Figure 9:
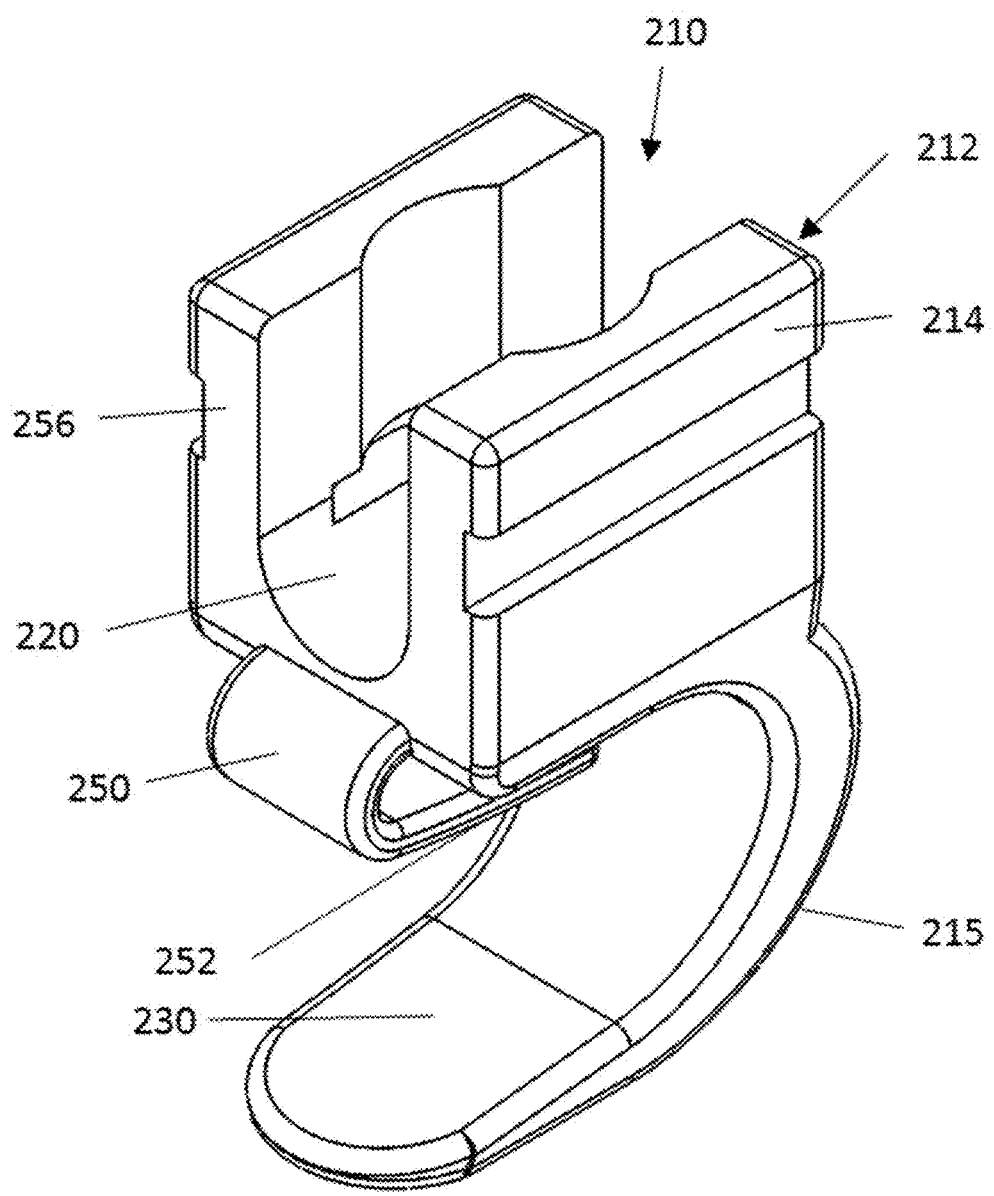
FIG. 9 is a perspective view of the third embodiment of the spinal fixation device illustrated in FIG. 8.

A third embodiment of a spinal fixation device is shown at 210 in FIGS. 8 and 9. The illustrated spinal fixation device 210 is similar to the spinal fixation device 10 and includes a hook base 212 having an upper portion 214 and a shoe portion 215. The upper portion 214 includes an aperture 254 formed in a forward-facing surface 256 of the upper portion 214 and having an axis substantially parallel with the channel 220. The illustrated shoe portion 215 includes a bone facing surface 230. If desired, the bone facing surface 230 may include ribs, such as the ribs 32 shown in FIGS. 1 through 5. The spinal fixation device 210 also includes spring member 250. The spring member 250 is substantially U-shaped and includes leg portions 252.

In the illustrated embodiment, one of the leg portions 252 is press-fit into the aperture 254. Alternatively, the spring member 250 may be attached to the spinal fixation device 210 by any desired means, such as with a threaded fastener, a rivet, or by welding.

In the illustrated embodiment, the spring member 250 is formed from shape memory material as described above. Alternatively, the spring member 250 may be formed from metal, such as stainless steel, or spring steel.

The spring member 250 is configured and positioned to exert a clamping force on a vertebra to which the shoe portion 215 is attached, thus preventing the spinal fixation device 210 from falling off the vertebra during implantation of the spinal fixation device 210 and subsequent attachment of the fusion rod 19. The spring member 250 may have any desired shape configured to exert a clamping force on a vertebra to which the shoe portion 215 will be attached.

As described above regarding the spring member 150, the spring member 250 will be pre-configured in a final engaged, closed or clamped shape and position, as shown in FIGS. 8 and 9, such that the spring member 250 will be in the engaged, closed or clamped position upon implantation. As the spinal fixation device 210 is implanted, the vertebra to which it is attached will engage the spring member 250 and urge the spring member 250 toward the upper portion 214. After implantation, the shape memory material spring member 250 will attempt to return to its original shape and position, i.e., the engaged, closed or clamped shape and position shown in FIGS. 8 and 9, thereby exerting a clamping force on the portion of the vertebra to which the spinal fixation device 210 is attached.

Figure 10:
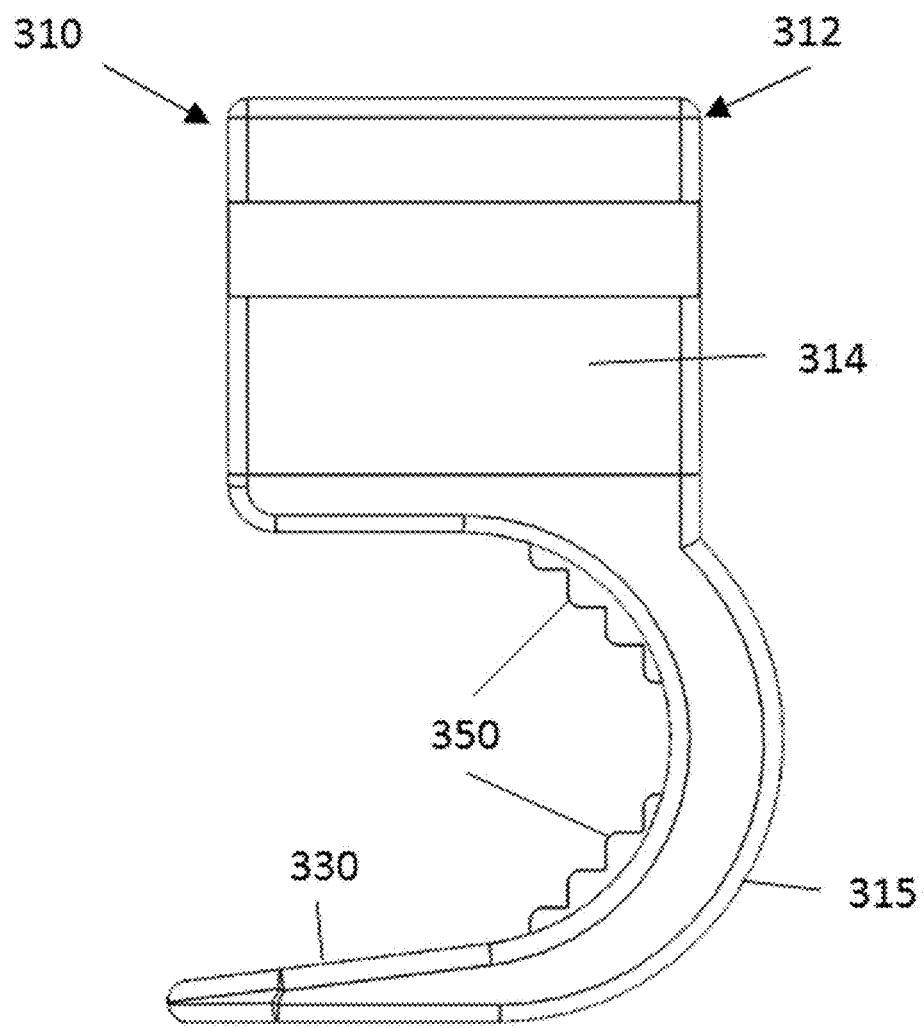
FIG. 10 is a side elevational view of a fourth embodiment of a spinal fixation device in accordance with this invention.

A fourth embodiment of a spinal fixation device is shown at 310 in FIG. 10. The illustrated spinal fixation device 310 is similar to the spinal fixation device 10 and includes a hook base 312 having an upper portion 314 and a shoe portion 315. The illustrated shoe portion 315 includes a bone facing surface 330. A plurality of teeth 350 extend radially outward of the surface 330. The teeth 350 have a substantially triangular cross-sectional shape and extend transversely across the surface 330 of the shoe portion 315. The teeth 350 may have any desired length less than or equal to a width of the shoe portion 315. Alternatively, the teeth 350 may have any desired shape configured to engage a vertebra to which the shoe portion 315 will be attached.

In the illustrated embodiment, the teeth 350 are integrally formed with the shoe portion 315. Alternatively, the teeth 350 may be attached to the shoe portion 315 by any desired means, such as with a threaded fastener, a rivet, by welding, or by press-fit attachment. In the illustrated embodiment, the teeth 350 are formed from the same material as the shoe portion 315, i.e., titanium or stainless steel.

In the illustrated embodiment, eight teeth 350 are illustrated. Alternatively, any desired number of teeth 350 may be provided, including a single tooth 350. The teeth 350 are configured and positioned to engage, grip, and/or anchor the shoe portion 315 in place relative to a vertebra to which the shoe portion 315 is attached, thus preventing the spinal fixation device 310 from falling off the vertebra during implantation of the spinal fixation device 310 and subsequent attachment of the fusion rod 19.

Figure 11:
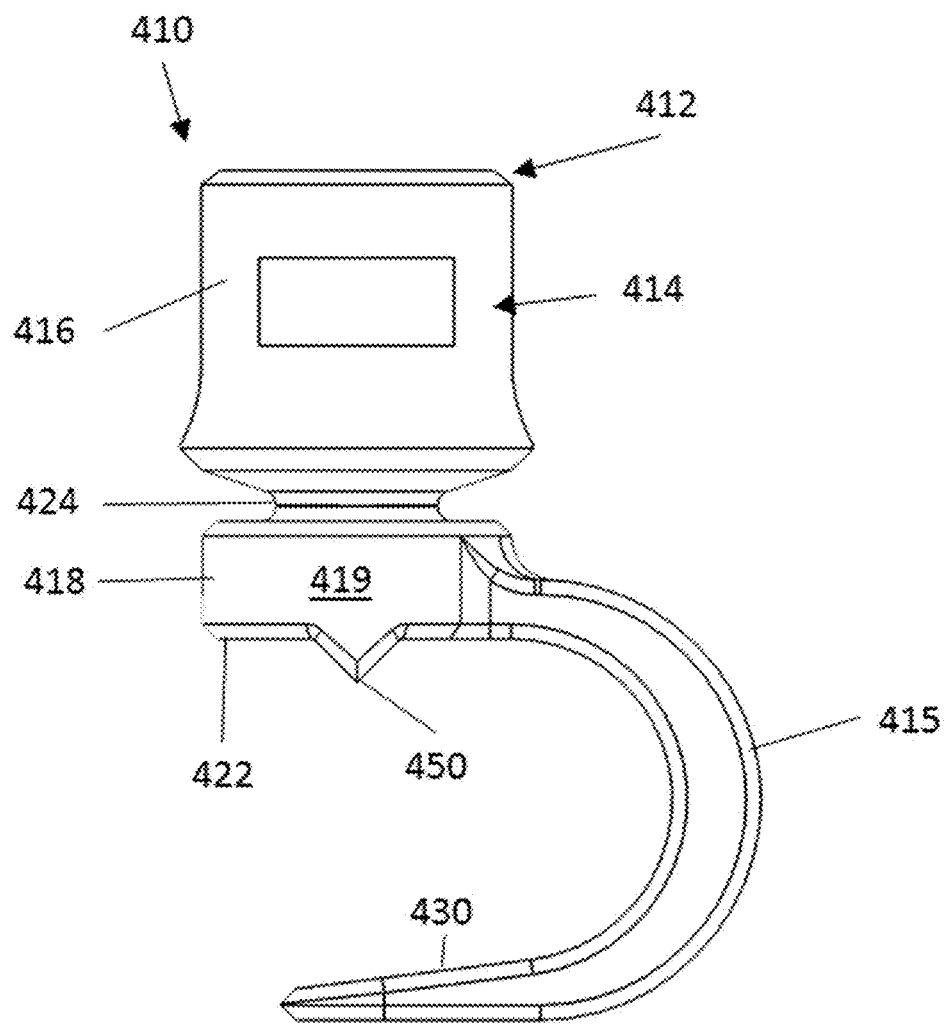
FIG. 11 is a side elevational view of a fifth embodiment of a spinal fixation device in accordance with this invention.
Figure 12:
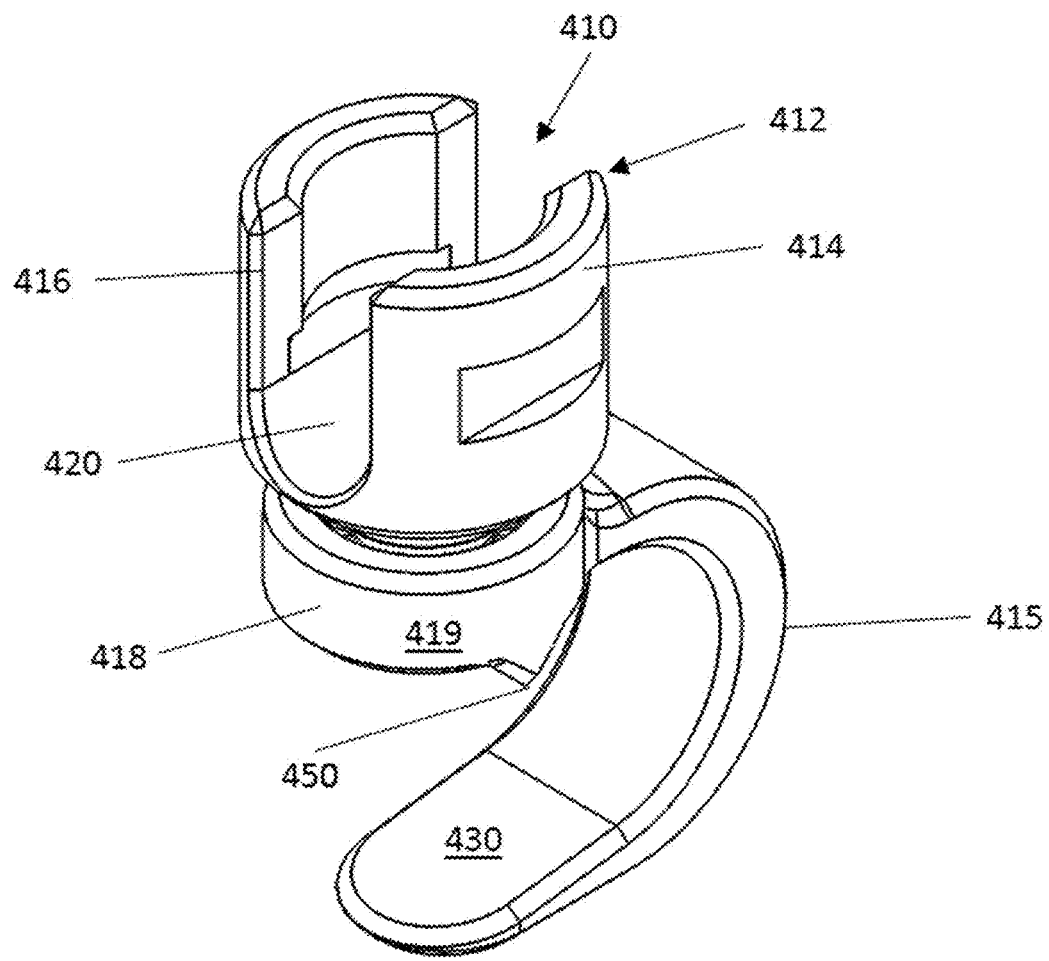
FIG. 12 is a perspective view of the fifth embodiment of the spinal fixation device illustrated in FIG. 11.

A fifth embodiment of a spinal fixation device is shown at 410 in FIGS. 11 and 12. The illustrated spinal fixation device 410 is similar to the spinal fixation device 10 and includes a hook base 412 having an upper portion 414 and a shoe portion 415. The illustrated shoe portion 415 includes a bone facing surface 430. Unlike the spinal fixation device 10 however, the upper portion 414 of the spinal fixation device 410 includes a first portion 416 having a channel 420 and a second or lower portion 418. The lower portion 418 has a substantially cylindrical outer side wall 419 and includes a bone facing surface 422. Alternatively, the outer side wall 419 of the lower portion 418 may have other shapes, such as for example rectangular or oval.

The first portion 416 and the lower portion 418 are connected by a joint 424 that allows poly-axial movement between the first portion 416 and the lower portion 418. In the illustrated embodiment, a ball joint connects the first portion 416 and the lower portion 418. Alternatively, any other joint that provides poly-axial movement between the first portion 416 and the lower portion 418 may be used.

A tooth 450 extends outward of the surface 422 of the lower portion 418. The tooth 450 has a substantially triangular cross-sectional shape and extends diametrically across the surface 422 opposite a portion of the bone facing surface 430 of the shoe portion 415. The tooth 450 may have any desired length less than or equal to a width or diameter of the lower portion 418. The tooth 450 may have any desired shape configured to engage a vertebra to which the shoe portion 415 will be attached The tooth 450 is integrally formed with the lower portion 418. Alternatively, the tooth 450 may be attached to the lower portion 418 by any desired means, such as with a threaded fastener, a rivet, by welding, or by press-fit attachment. In the illustrated embodiment, the tooth 450 is formed from the same material as the lower portion 418, i.e., titanium or stainless steel.

In the illustrated embodiment, a single tooth 450 is illustrated. Alternatively, any desired number of teeth 450 may be provided. The tooth 450 is configured and positioned to engage, grip, and/or anchor the spinal fixation device 410 in place relative to a vertebra to which the shoe portion 415 is attached, thus preventing the spinal fixation device 410 from falling off the vertebra during implantation of the spinal fixation device 410 and subsequent attachment of the fusion rod 19.

Figure 13:
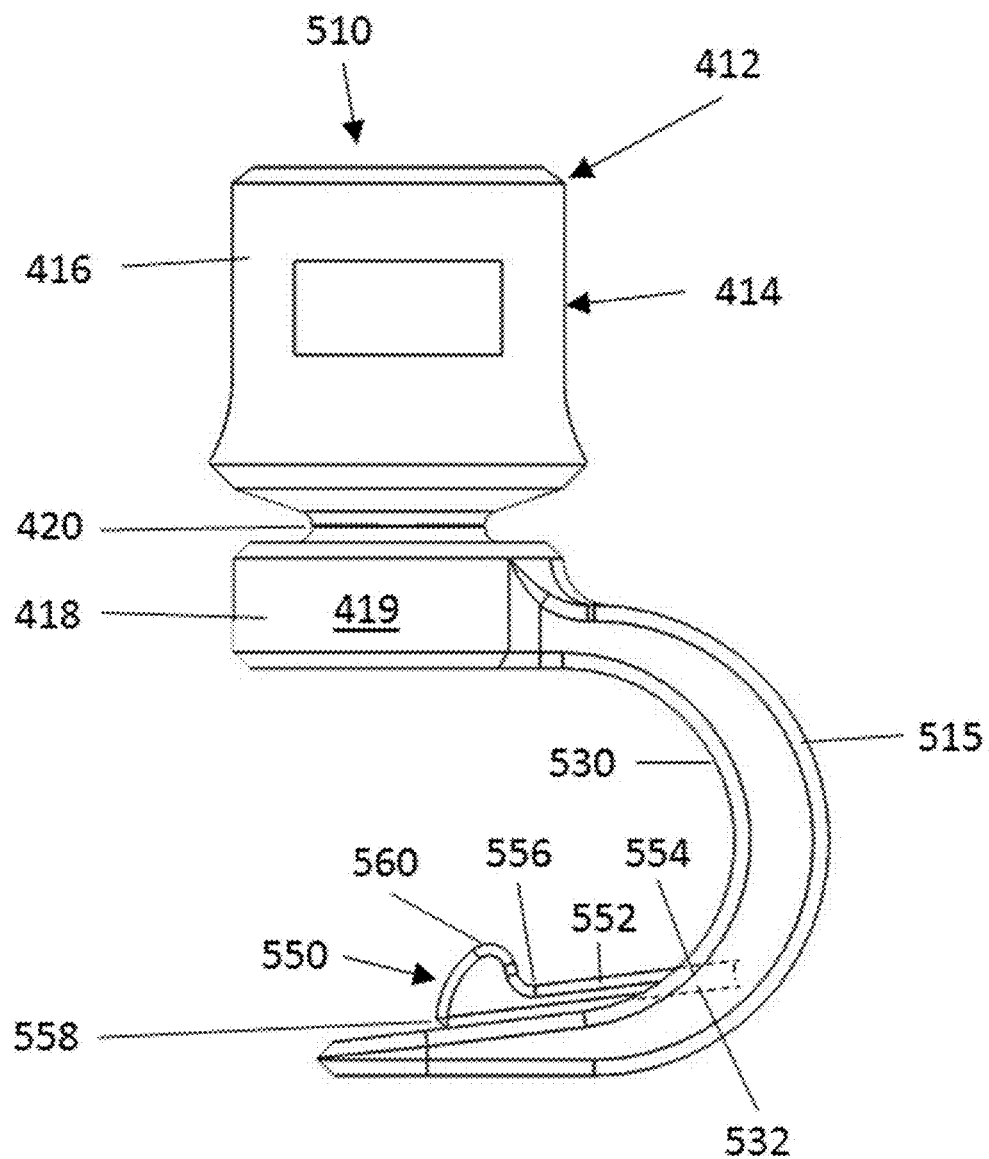
FIG. 13 is a side elevational view of a sixth embodiment of a spinal fixation device in accordance with this invention.
Figure 14:
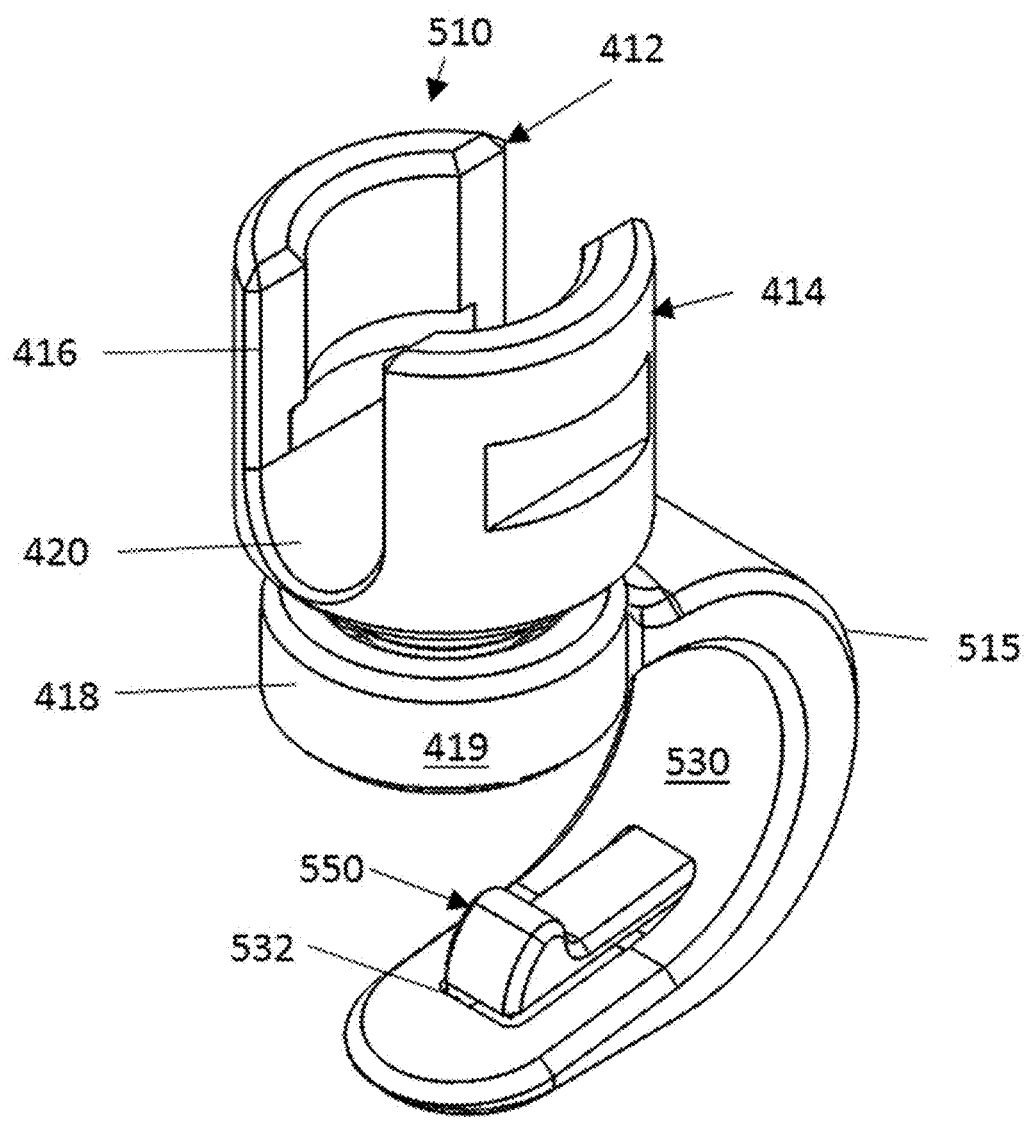
FIG. 14 is a perspective view of the sixth embodiment of the spinal fixation device illustrated in FIG. 13.

A sixth embodiment of a spinal fixation device is shown at 510 in FIGS. 13 and 14. The illustrated spinal fixation device 510 is similar to the spinal fixation device 410 and includes the hook base 412, upper portion 414, and a shoe portion 515. The upper portion 414 includes the first portion 416 and the lower portion 418. The lower portion 418 however, does not include a tooth as shown in FIGS. 11 and 12. The first portion 416 and the lower portion 418 are connected by a joint that allows poly-axial movement between the first portion 416 and the lower portion 418, such as the joint 424 described above.

The illustrated shoe portion 515 includes a bone facing surface 530. An elongated groove 532 is formed in the surface 530. A spring member 550 includes an elongated body 552 having a first end 554, a bone engaging surface 556, and a second end 558. A detent portion 560 extends outward of the surface 556 at the second end 558. In the illustrated embodiment, a single outwardly extending detent portion 560 is shown. Alternatively, any desired number of detent portions may be provided. Alternatively, the spring member 550 may also be formed without a detent portion.

The spring member 550 is attached within the groove 532 in the shoe portion 515 in a cantilevered fashion such that the first end 553 is press-fit in the groove 532 and the second end 558 of the spring member 550 is spaced a distance apart from a bottom surface of the groove 532.

The spring member 550 may also be attached to the shoe portion 515 by any desired means, such as with a threaded fastener, a rivet, or by welding. In the illustrated embodiment, the spring member 550 is formed from shape memory material as described above. Alternatively, the spring member 550 may be formed from metal, such as stainless steel, or spring steel.

In the illustrated embodiment, a single spring member 550 is illustrated. Alternatively, more than one spring member 550 may be provided. The spring member 550 is configured and positioned to exert a clamping force on a vertebra to which the shoe portion 515 is attached, thus preventing the spinal fixation device 510 from falling off the vertebra during implantation of the spinal fixation device 510 and subsequent attachment of the fusion rod 19.

As described above regarding a second embodiment of the clamp 16, the spring member 550 will be pre-configured in a final engaged, closed or clamped shape and position, as shown in FIGS. 13 and 14, such that the spring member 550 will be in the engaged, closed or clamped position upon implantation. As the spinal fixation device 510 is implanted, the vertebra to which it is attached will engage the spring member 550 and urge the spring member 550 toward the shoe portion 515. After implantation, the shape memory material spring member 550 will attempt to return to its original shape and position, i.e., the engaged, closed or clamped position shown in FIGS. 13 and 14, thereby exerting a clamping force on the portion of the vertebra to which the spinal fixation device 510 is attached.

Alternatively, the desired clamping force on the vertebra to which the shoe portion 515 is attached may be achieved by a spring member 550 formed from metal, such as stainless steel, or spring steel.

Figure 15:
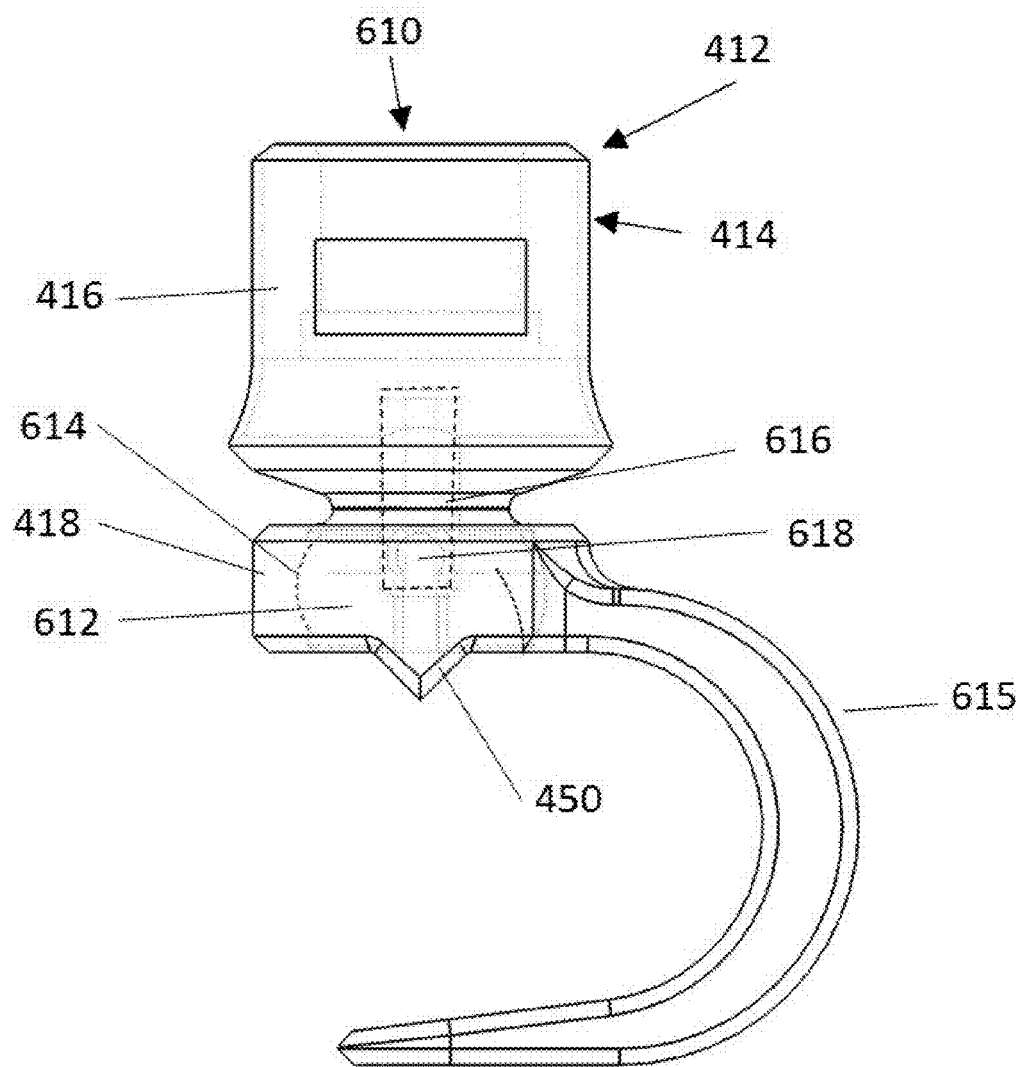
FIG. 15 is an enlarged side elevational view of a portion of a seventh embodiment of a spinal fixation device in accordance with this invention.

A seventh embodiment of a spinal fixation device is shown at 610 in FIG. 15. The illustrated spinal fixation device 610 is similar to the spinal fixation device 410 shown in FIGS. 11 and 12 and includes the hook base 412, upper portion 414, and shoe portion 415. The upper portion 414 includes the first portion 416 and the lower portion 418. In the illustrated embodiment, the lower portion 418 is shown with the tooth 450. Alternatively, the spinal fixation device 610 may be formed without the tooth 450.

The first portion 416 includes a ball portion 612 mounted within a semi-spherical socket 614 of the lower portion 418. A longitudinally extending pin bore 616 is centrally formed through the ball portion 612. The spinal fixation device 610 may be locked whereby movement of the first portion 416 relative to the lower portion 418 is prevented by insertion of a locking pin 618 into the pin bore 616. The illustrated locking pin 618 is substantially cylindrical and may have an outside diameter slightly larger than an inside diameter of the pin bore 616. When the locking pin 618 is inserted into the pin bore 616, an outside surface of the ball portion 612 is caused to expand slightly radially outwardly. This outward radial expansion creates a frictional force on the inside surface of the socket 614, and prevents further movement of the first portion 416 relative to the lower portion 418. The locking pin 618 may be held in place in the pin bore 616 by the fusion rod 19 when installed such as shown in FIG. 2.

Figure 16:
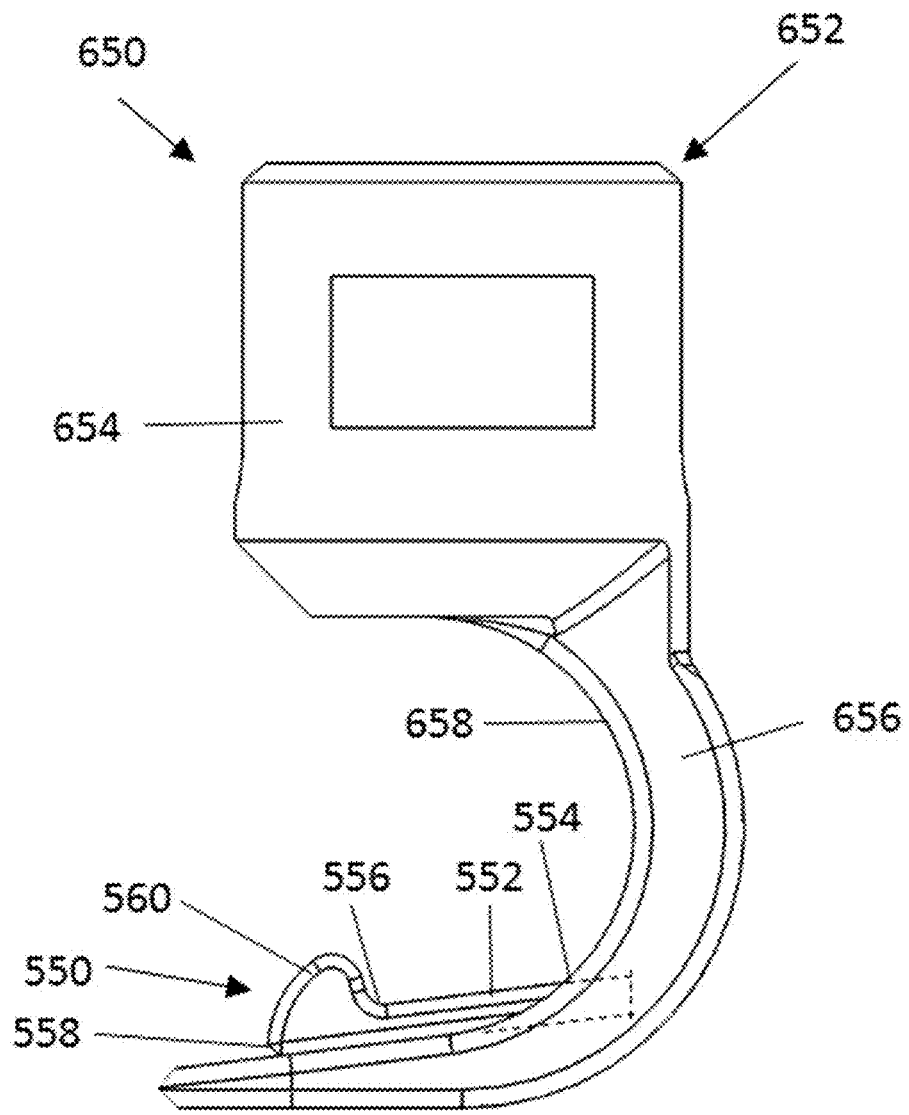
FIG. 16 is a side elevational view of an eighth embodiment of a spinal fixation device in accordance with this invention.
Figure 17:
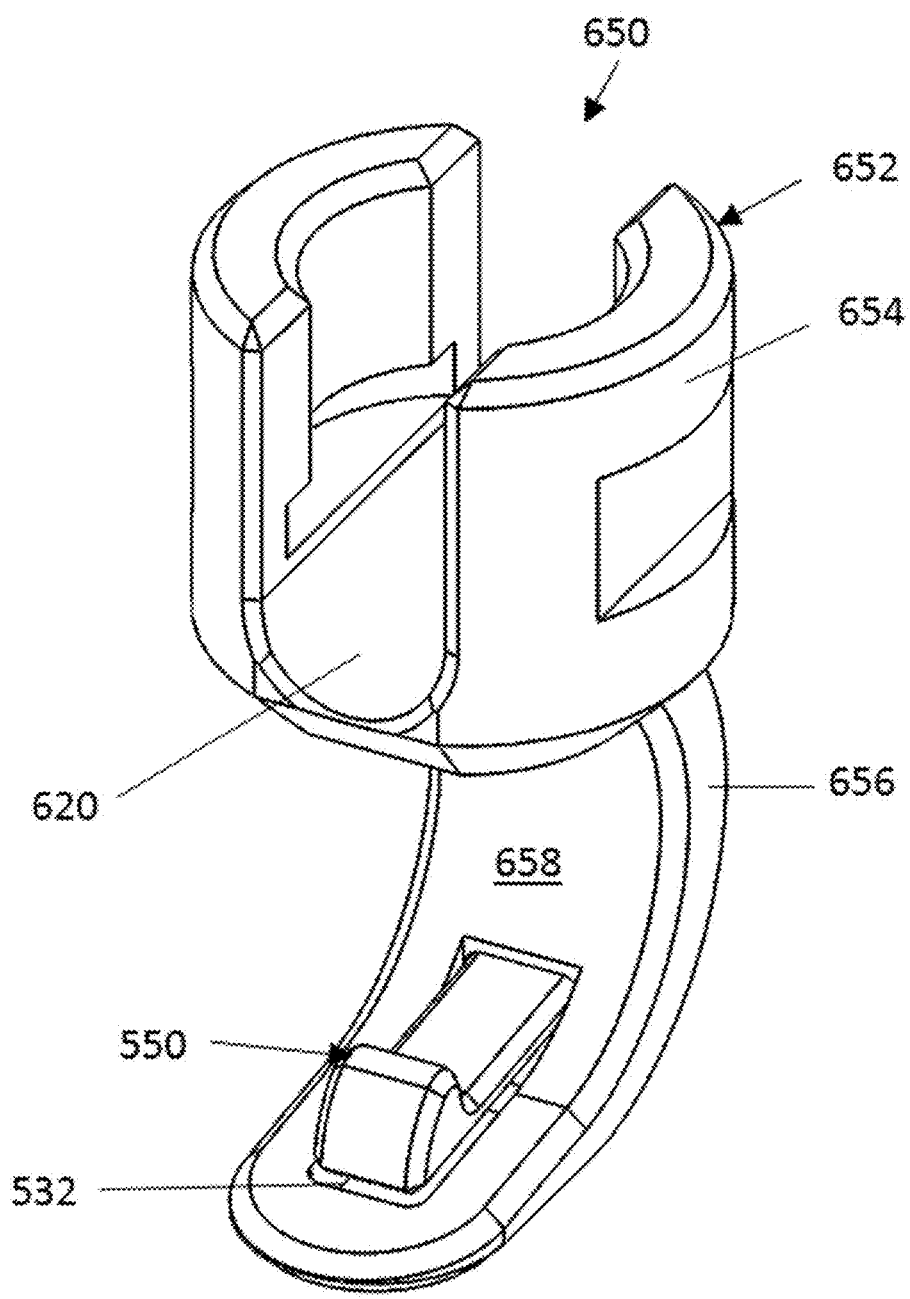
FIG. 17 is a perspective view of the eighth embodiment of the spinal fixation device illustrated in FIG. 16.

An eighth embodiment of a spinal fixation device is shown at 650 in FIGS. 16 and 17. The illustrated spinal fixation device 650 is similar to the spinal fixation device 110 and includes a hook base 652 having an upper portion 654, and a shoe portion 656. The upper portion 654 includes a channel 620. The shoe portion 656 is similar to the shoe portion 515 shown in FIGS. 13 and 14. The illustrated shoe portion 656 includes a bone facing surface 658 having the elongated groove 532 formed therein. The spring member 550, described in detail above, is attached within the groove 532 in the shoe portion 656.

Figure 18:
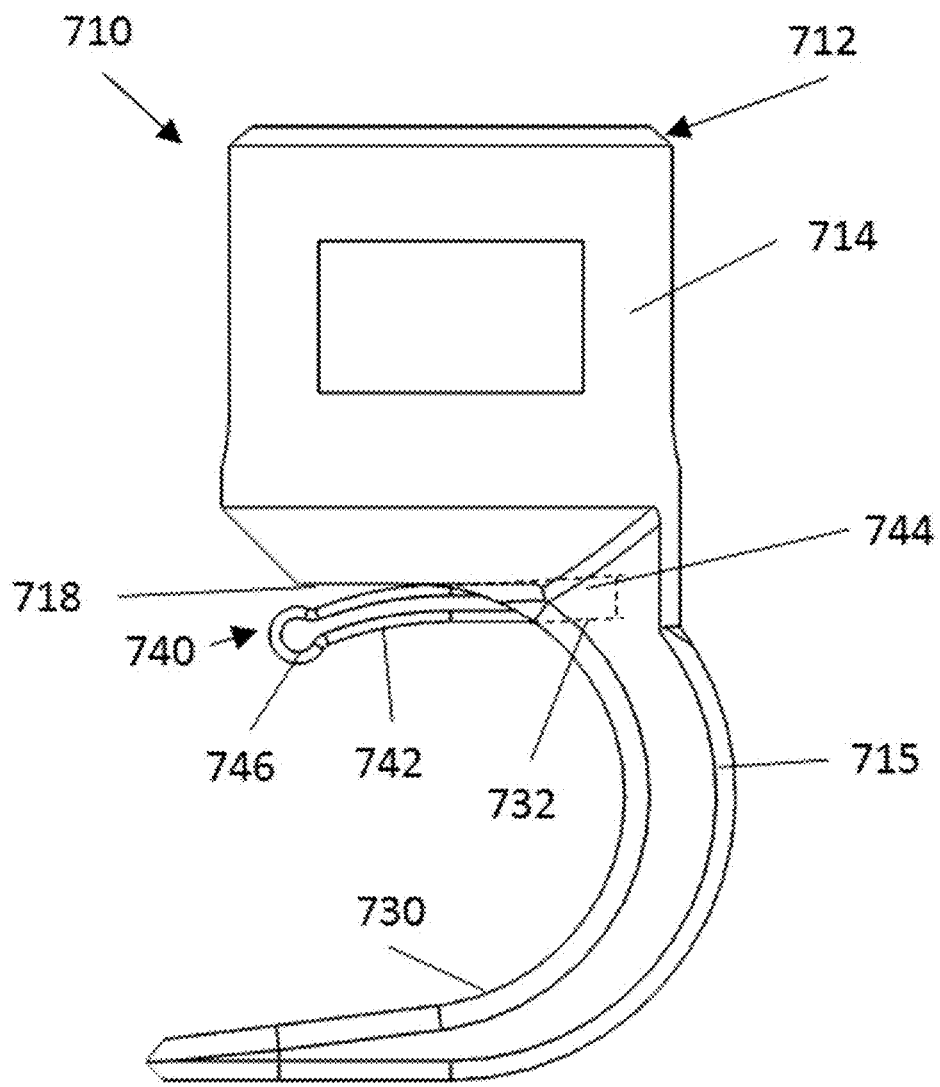
FIG. 18 is a side elevational view of a ninth embodiment of a spinal fixation device in accordance with this invention.
Figure 19:
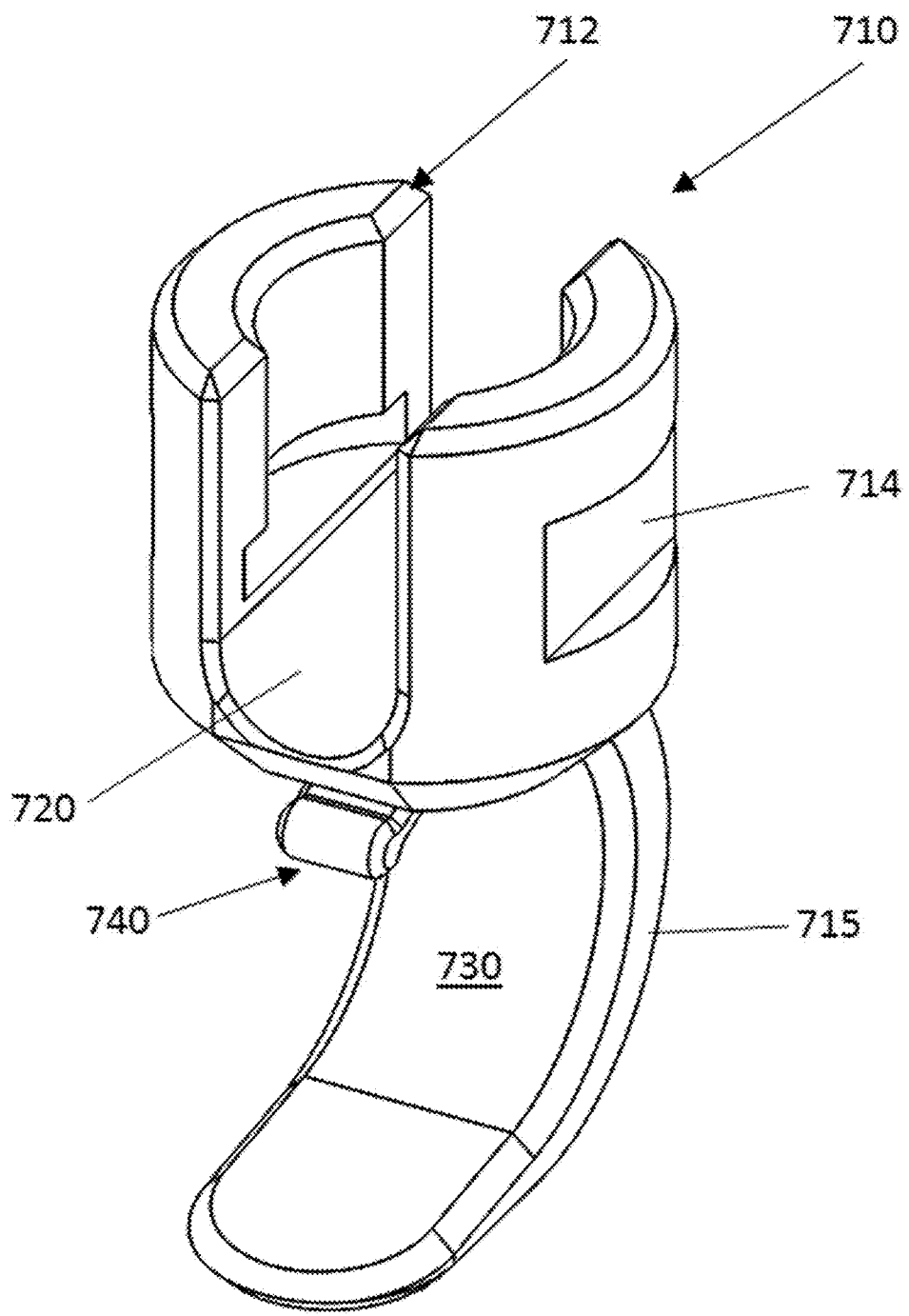
FIG. 19 is a perspective view of the ninth embodiment of the spinal fixation device illustrated in FIG. 18.

A ninth embodiment of a spinal fixation device is shown at 710 in FIGS. 18 and 19. The illustrated spinal fixation device 710 is similar to the spinal fixation device 110 and includes a hook base 712 having an upper portion 714 and a shoe portion 715. The upper portion 714 includes a channel 720. The illustrated shoe portion 715 includes a bone facing surface 730. An aperture 732 is formed in an upper portion of the shoe-facing surface 730 adjacent a shoe-facing surface 718 of the upper portion 714.

The spinal fixation device 710 also includes spring member 740. The spring member 740 includes an elongated body 742 having a first end 744 and a second end 746. In the illustrated embodiment, the body 742 has an arcuate shape. Alternatively, the body 742 may have another shape, such as for example substantially straight. The second end of the 746 may have a thickness greater than a thickness of the body 742. In the illustrated embodiment, the second end 746 of the spring member 740 has semi-cylindrical shape. Alternatively, the second end 746 of the spring member 740 may have other shapes, such as for example the shape of the detent portion 560 shown in FIGS. 13 and 14.

The spring member 740 is attached within the aperture 732 in the shoe portion 715 in a cantilevered fashion such that the second end 746 of the spring member 740 is spaced a distance apart from the shoe-facing surface 718 of the upper portion 714. The spring member 740 may also be attached to the shoe portion 715 by any desired means, such as with a threaded fastener, a rivet, or by welding.

In the illustrated embodiment, the spring member 740 is formed from shape memory material as described above. Alternatively, the spring member 550 may be formed from metal, such as stainless steel, or spring steel.

In the illustrated embodiment, a single spring member 740 is illustrated. Alternatively, more than one spring member 740 may be provided. The spring member 740 is configured and positioned to exert a clamping force on a vertebra to which the shoe portion 715 is attached, thus preventing the spinal fixation device 710 from falling off the vertebra during implantation of the spinal fixation device 710 and subsequent attachment of the fusion rod 19.

As described above regarding a second embodiment of the spring member 550, the spring member 740 will be pre-configured in a final engaged, closed or clamped shape and position, as shown in FIGS. 18 and 19, such that the spring member 740 will be in the engaged, closed or clamped position upon implantation. As the spinal fixation device 710 is implanted, the vertebra to which it is attached will engage the spring member 740 and urge the spring member 740 toward the shoe-facing surface 718 of the upper portion 714. After implantation, the shape memory material spring member 740 will attempt to return to its original shape and position, i.e., the engaged, closed or clamped position shown in FIGS. 18 and 19, thereby exerting a clamping force on the portion of the vertebra to which the spinal fixation device 710 is attached.

Alternatively, the desired clamping force on the vertebra to which the shoe portion 5715 is attached may be achieved by a spring member 740 formed from metal, such as stainless steel, or spring steel.

Figure 20:
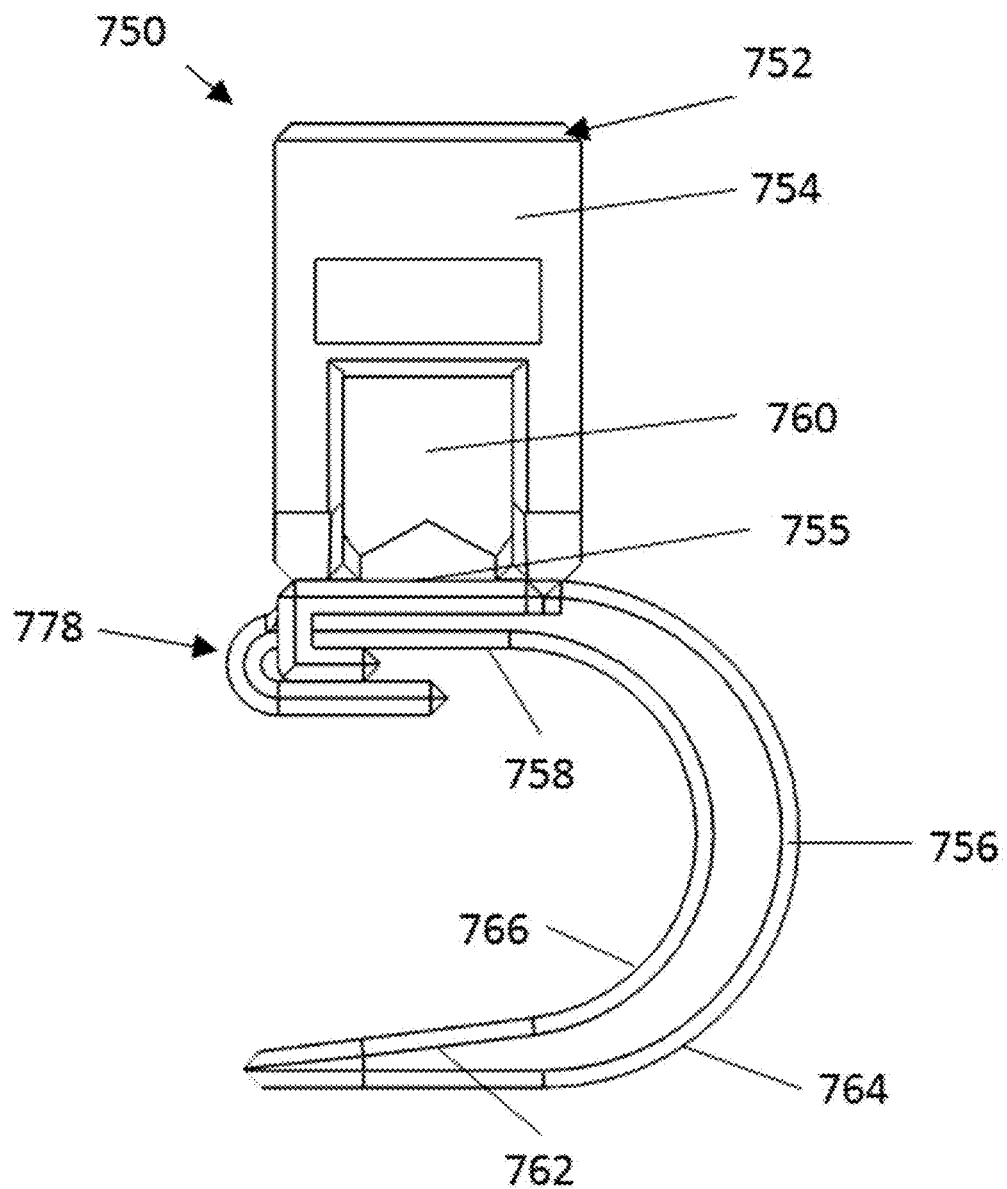
FIG. 20 is a side elevational view of a tenth embodiment of a spinal fixation device in accordance with this invention.
Figure 21:
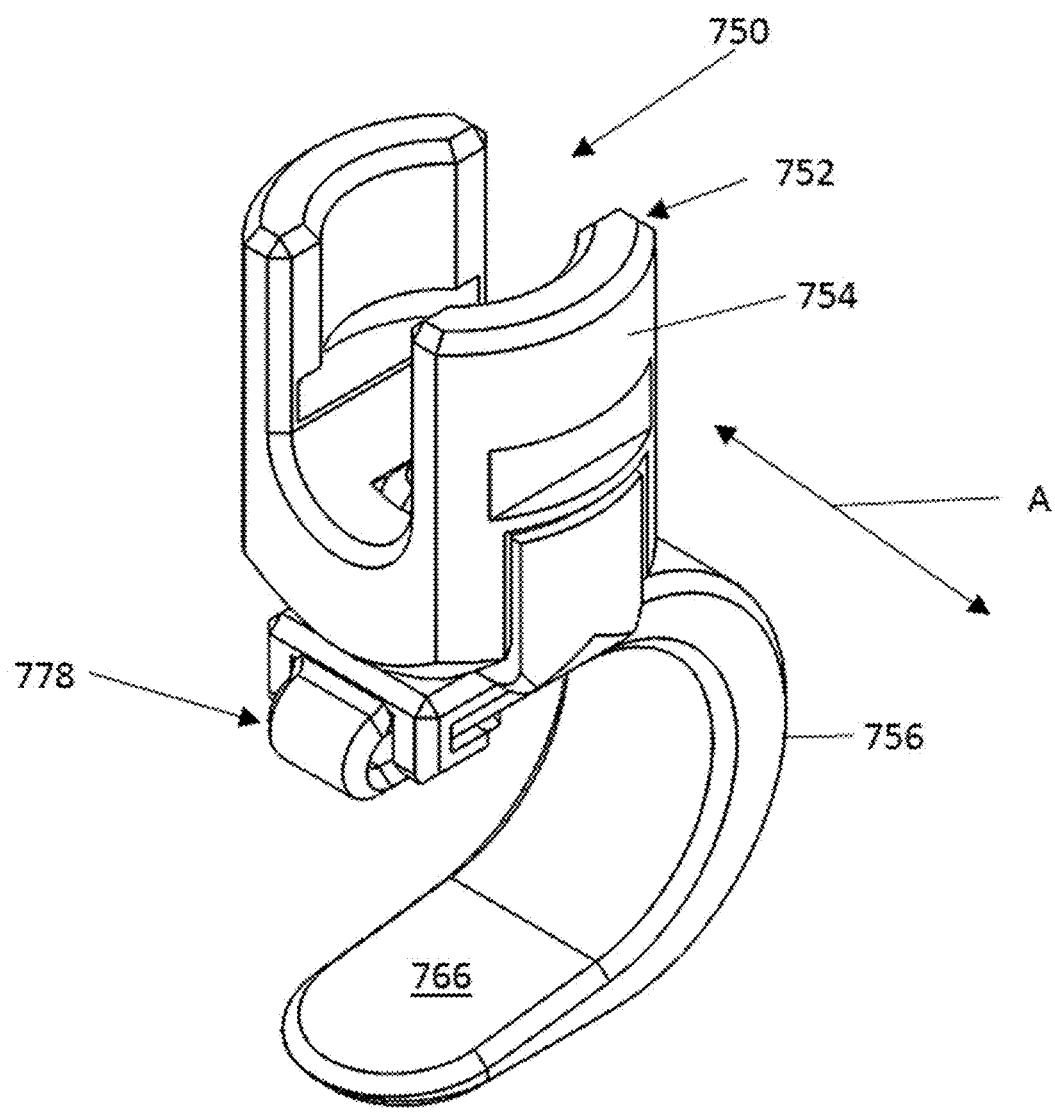
FIG. 21 is a perspective view of the tenth embodiment of the spinal fixation device illustrated in FIG. 20.

A tenth embodiment of a spinal fixation device is shown at 750 in FIGS. 20 and 21. The illustrated spinal fixation device 750 is similar to the spinal fixation device 10 and includes a hook base 752 having an upper portion 754 and a shoe portion 756. The upper portion 754 includes a shoe facing surface 755 and a mounting bracket 760.

Figure 20A:
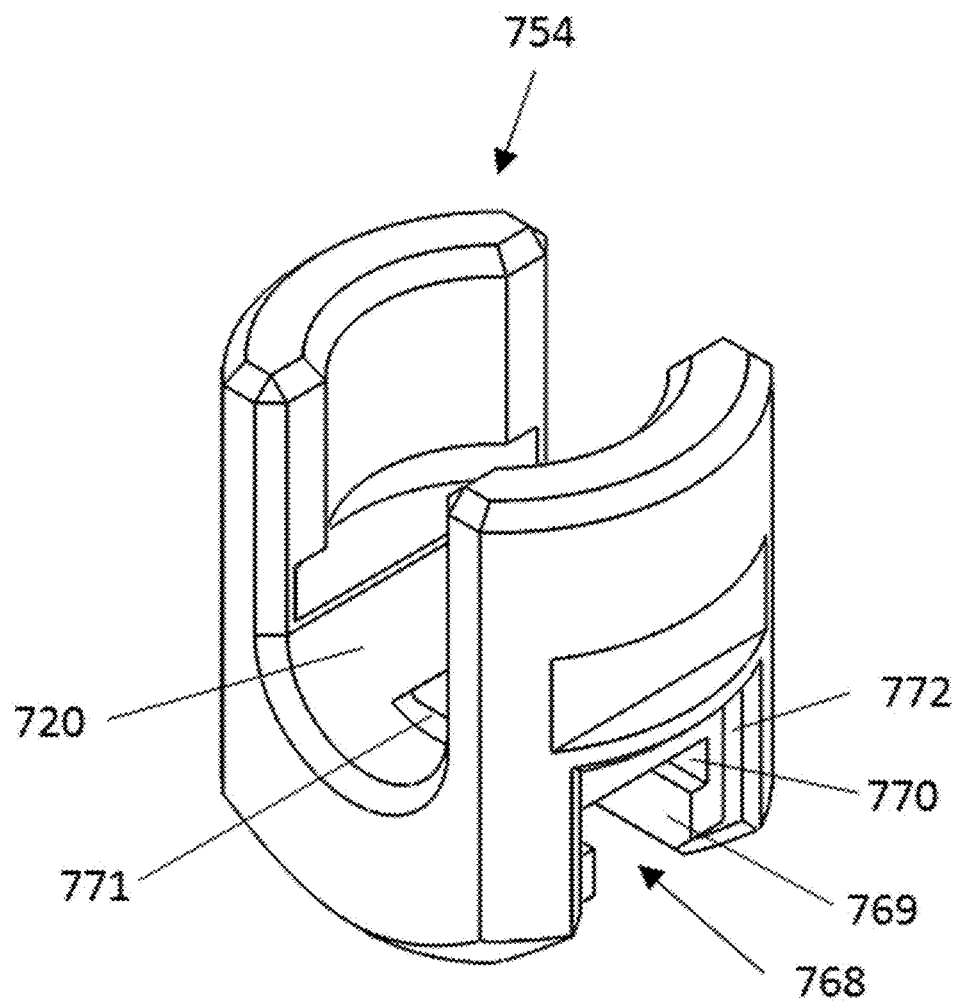
FIG. 20A is an enlarged perspective view of the upper portion of the hook base illustrated in FIGS. 20 and 21.

Referring to FIG. 20A, the upper portion 754 of the hook base 752 is shown with the mounting bracket 760 removed. A post slot 768 is formed in the shoe facing surface 755 and extends through the upper portion 754 substantially perpendicularly to the axis of the channel 720. The post slot 768 includes a body portion 769 and a head portion 770. The head portion 770 has a width larger than a width of the body portion 769. A pin access slot 771 is formed between the channel 720 and the head portion 770 of the post slot 768. A substantially rectangular mounting bracket notch 772 is formed in an outside surface of the upper portion 754 about both ends of the post slot 768. The purpose of the post slot 768 and the pin access slot 771 will be explained in detail below.

Figure 20B:
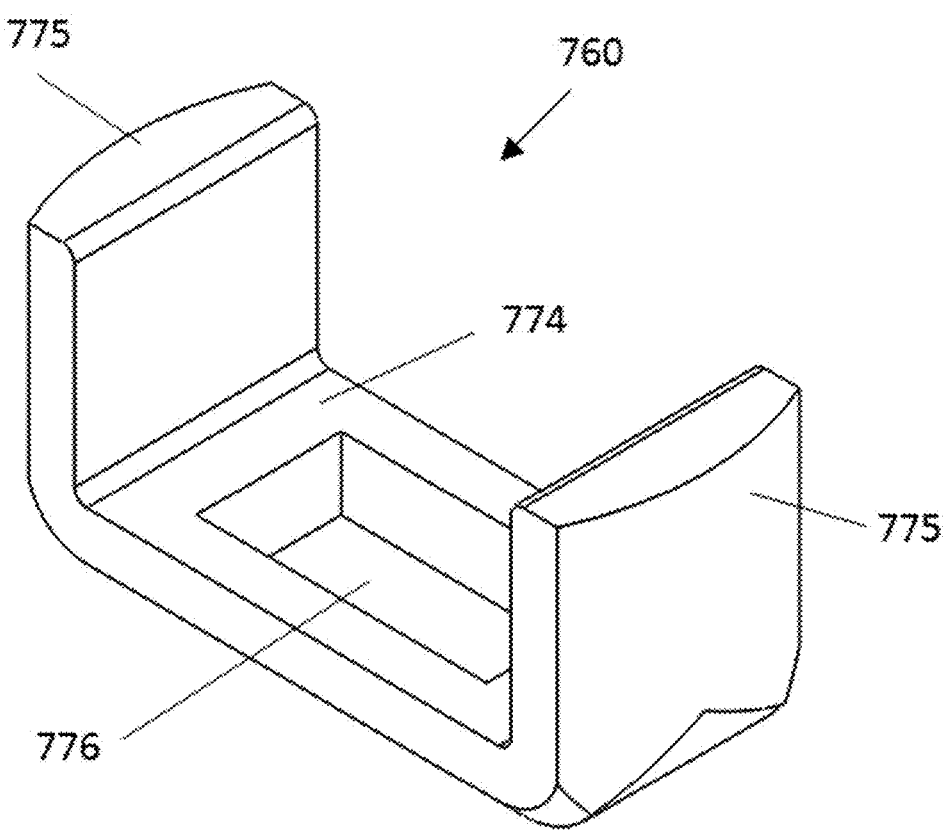
FIG. 20B is an enlarged perspective view of a portion of the mounting bracket illustrated in FIGS. 20 and 21.

Referring to FIG. 20B, the mounting bracket 760 is shown removed from the upper portion 754. The illustrated mounting bracket 760 includes a base 774 and two outwardly extending side walls 775. A translation slot 776 is formed through the base 774. The illustrated translation slot 776 is rectangular. Alternatively, the translation slot 776 may have other shapes, such as oval.

The illustrated shoe portion 756 is substantially U-shaped having a first leg 758 adjacent the hook base 752, a second leg 762, an outside surface 764, and a bone facing surface 766. A spring assembly 778 is attached to a distal end of the first leg 758.

Figure 20C:
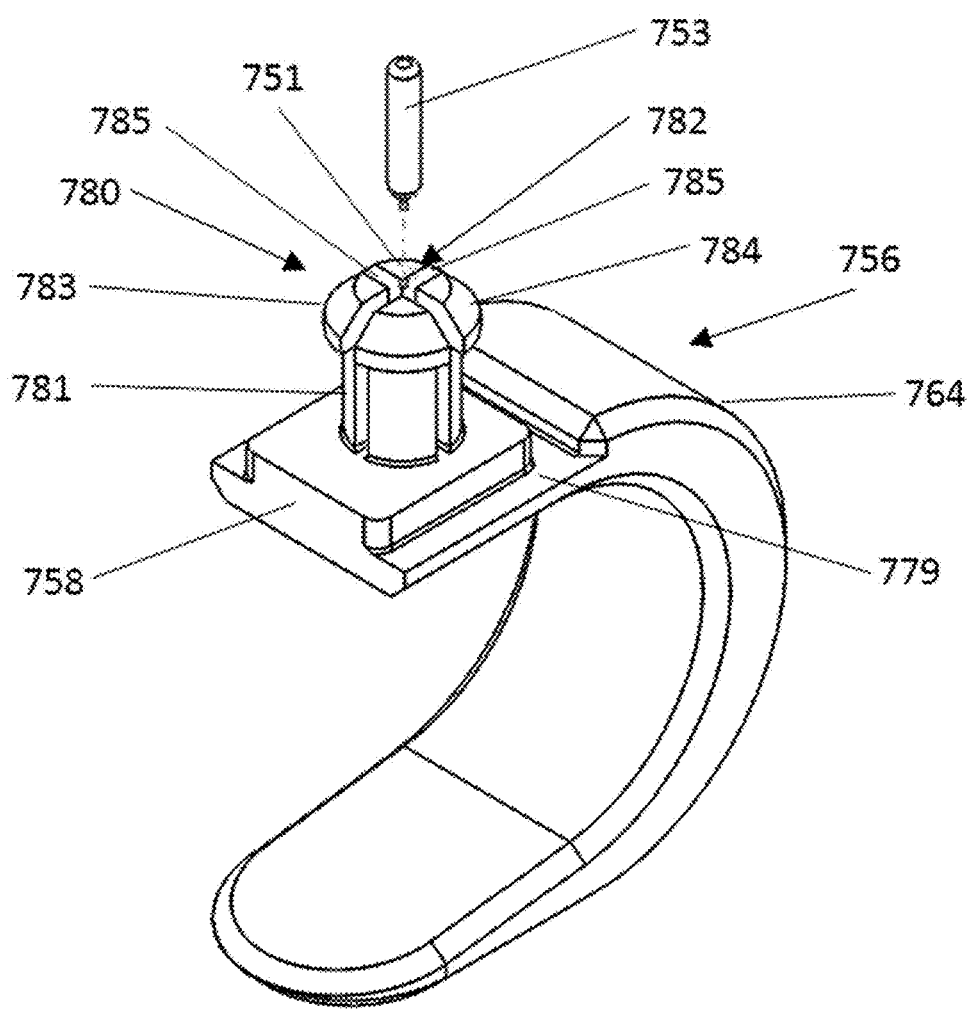
FIG. 20C is an enlarged perspective view of a portion of the shoe portion illustrated in FIGS. 20 and 21.

Referring to FIG. 20C, a substantially U-shaped channel 779 is formed in the outside surface 764 of the first leg 758 of the shoe portion 756. A mounting post 780 extends outward of the outside surface 764 between a distal end of the first leg 758 and a base of the U-shaped channel 779. The post 780 includes a body 781 having a substantially cylindrical outer surface and head 782 having a first, substantially cylindrical outer surface 783 and a second, tapered outer surface 784 extending between the first outer surface 783 and a distal end of the post 780. An outside diameter of the outer surface 783 of the head 782 is larger than an outside diameter of the body 781. The illustrated post 780 is formed in quarters defined by longitudinally extending channels 785 formed through the post 780. The intersection of the channels 785 defines a pin bore 751.

Figure 20D:
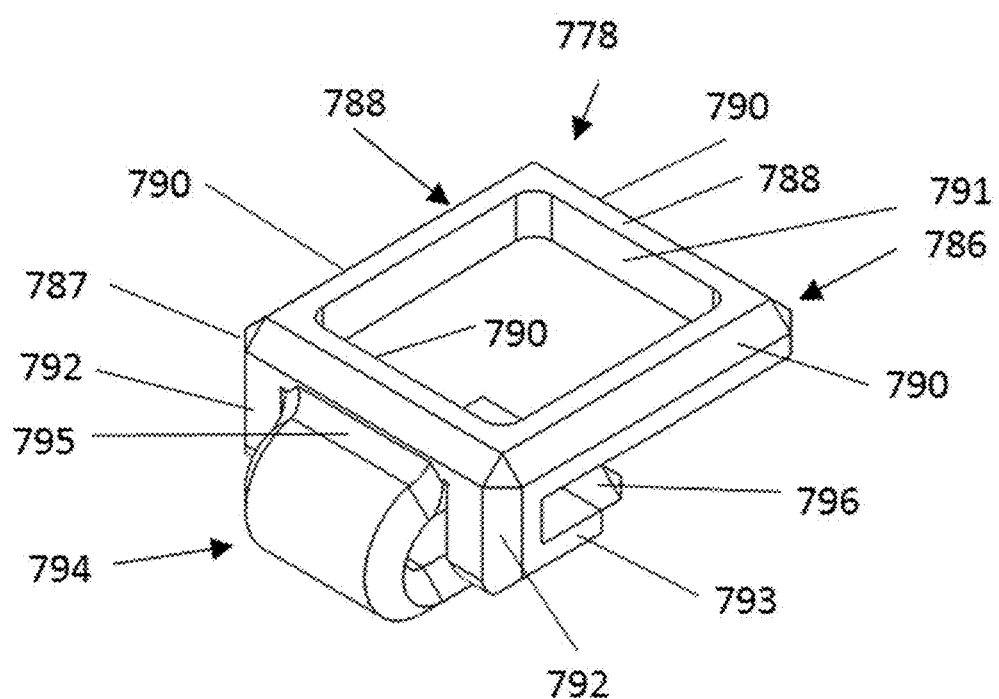
FIG. 20D is an enlarged perspective view of a portion of the spring assembly illustrated in FIGS. 20 and 21.

Referring to FIG. 20D, the spring assembly 778 is shown removed from the shoe portion 756. The illustrated spring assembly 778 includes a mounting bracket 760 having a first end 787 and a second end 788. An upper portion 789 of the mounting bracket 760 has four sides 790 defining substantially rectangular opening 791. First legs 792 extend outward (downwardly when viewing FIG. 20D) from corners at the first end 787 of the upper portion 789. Second legs 793 extend inwardly from the first legs 792 and are substantially parallel with the sides 790. A substantially J-shaped spring 794 includes a first leg portion 795 extending outward of the first end 787 of the mounting bracket 760. A second leg portion 796 extends inwardly toward the bone facing surface 766 of the shoe portion 756 substantially parallel with the sides 790, and below and between the second legs 793 of the mounting bracket 760. The purpose of the spring 794 will be described in detail below.

In the illustrated embodiment, the spring 794 is integrally formed with the mounting bracket 760. Alternatively, the spring 794 may be separately formed and attached to the mounting bracket 760 by any means, such as by press fit or welding, or with a threaded fastener or a rivet.

In the illustrated embodiment, the spring 794 is formed from shape memory material as described above. Alternatively, the spring 794 may be formed from metal, such as stainless steel, or spring steel.

The spring 794 is configured and positioned to exert a clamping force on a vertebra to which the shoe portion 756 is attached, thus preventing the spinal fixation device 750 from falling off the vertebra during implantation of the spinal fixation device 750 and subsequent attachment of the fusion rod 19. The spring 794 may have any desired shape configured to exert a clamping force on a vertebra to which the shoe portion 756 will be attached.

As described above regarding the spring member 150, the spring 794 will be pre-configured in a final engaged, closed or clamped shape and position, as shown in FIGS. 20, 21, and 20D, such that the spring 794 will be in the engaged, closed or clamped position upon implantation. As the spinal fixation device 750 is implanted, the vertebra to which it is attached will engage the spring 794 and urge the spring 794 toward the upper portion 754. After implantation, the shape memory material spring 794 will attempt to return to its original shape and position, i.e., the engaged, closed or clamped shape and position shown in FIGS. 20, 21, and 20D, thereby exerting a clamping force on the portion of the vertebra to which the spinal fixation device 750 is attached.

When assembled the sides 790 of the mounting bracket 760 are press fit within the channel 779. The side walls 775 of the mounting bracket 760 press fit within the mounting bracket notches 772 of the upper portion 754. The mounting post 780 extends through the translation slot 776 of the mounting bracket 760 such that the post head 782 is within the head portion 770 of the post slot 768 and the post body 781 is within the body portion 769 of the post slot 768 and the translation slot 776 of the mounting bracket 760.

Translational or sliding movement of the upper portion 754 relative to the shoe portion 756 is possible in the direction of the Arrow A in FIG. 21. For example, the shoe portion 756 may be moved relative to the upper portion 754 urging the shoe portion 756 in the direction of the Arrow A, thereby causing the post body 781 to move longitudinally within the translation slot 776 and a body portion 769 of the post slot 768, and the post head 782 to move within the head portion 770 of the post slot 768.

Once a desired position of the upper portion 754 relative to the shoe portion 756 has been achieved by the surgeon, their positions may be fixed with a locking pin 753, shown in FIG. 20C. The illustrated locking pin 753 is substantially cylindrical and may have an outside diameter slightly larger than an inside diameter of the pin bore 751. When the locking pin 753 is inserted into the pin bore 751 through the pin access slot 771, the post head 782 and post body 781 are caused to move slightly radially outwardly. This outward radial movement creates a frictional force between the post head 782 and post body 781 and the inside surfaces of the head portion and the 770 body portion 769, respectively, of the post slot 768, and prevents further movement of the shoe portion 756 relative to the upper portion 754.

Figure 22:
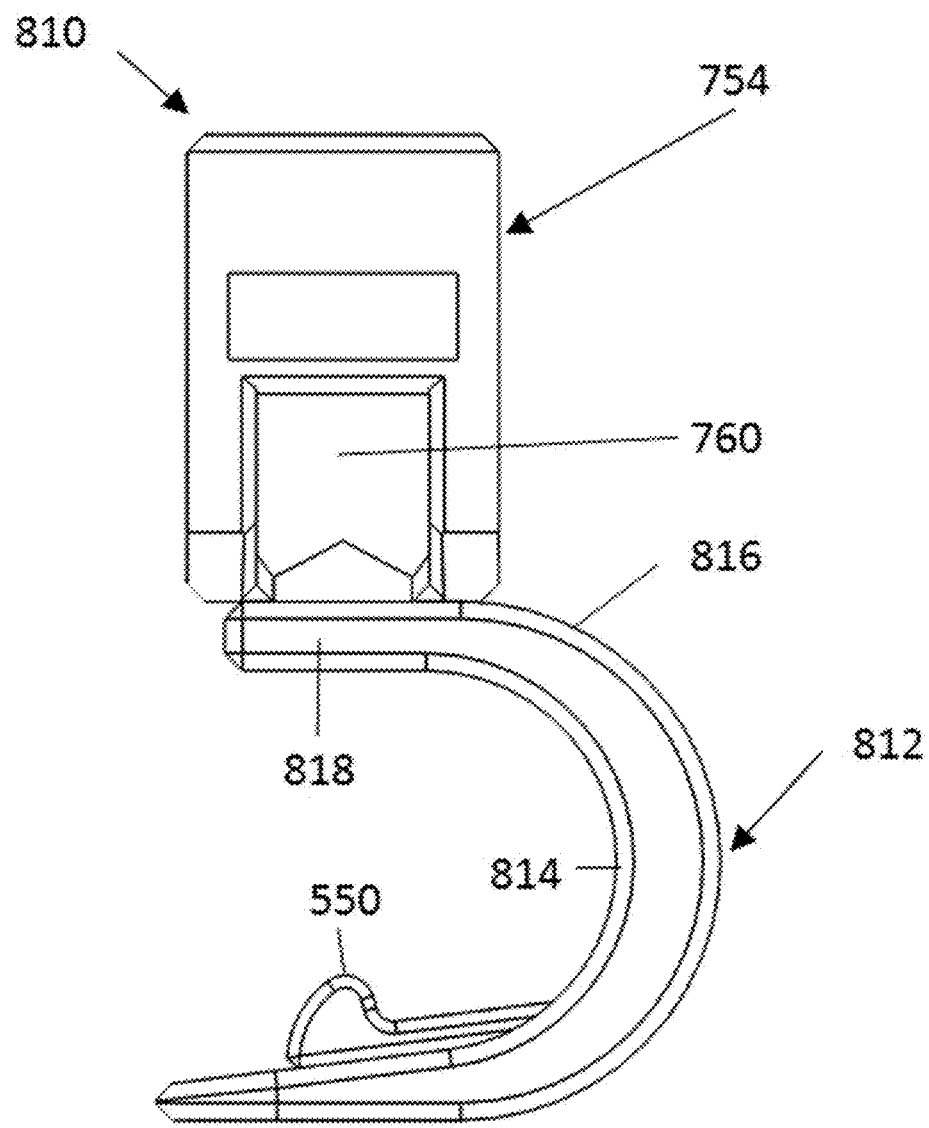
FIG. 22 is a side elevational view of an eleventh embodiment of a spinal fixation device in accordance with this invention.
Figure 23:
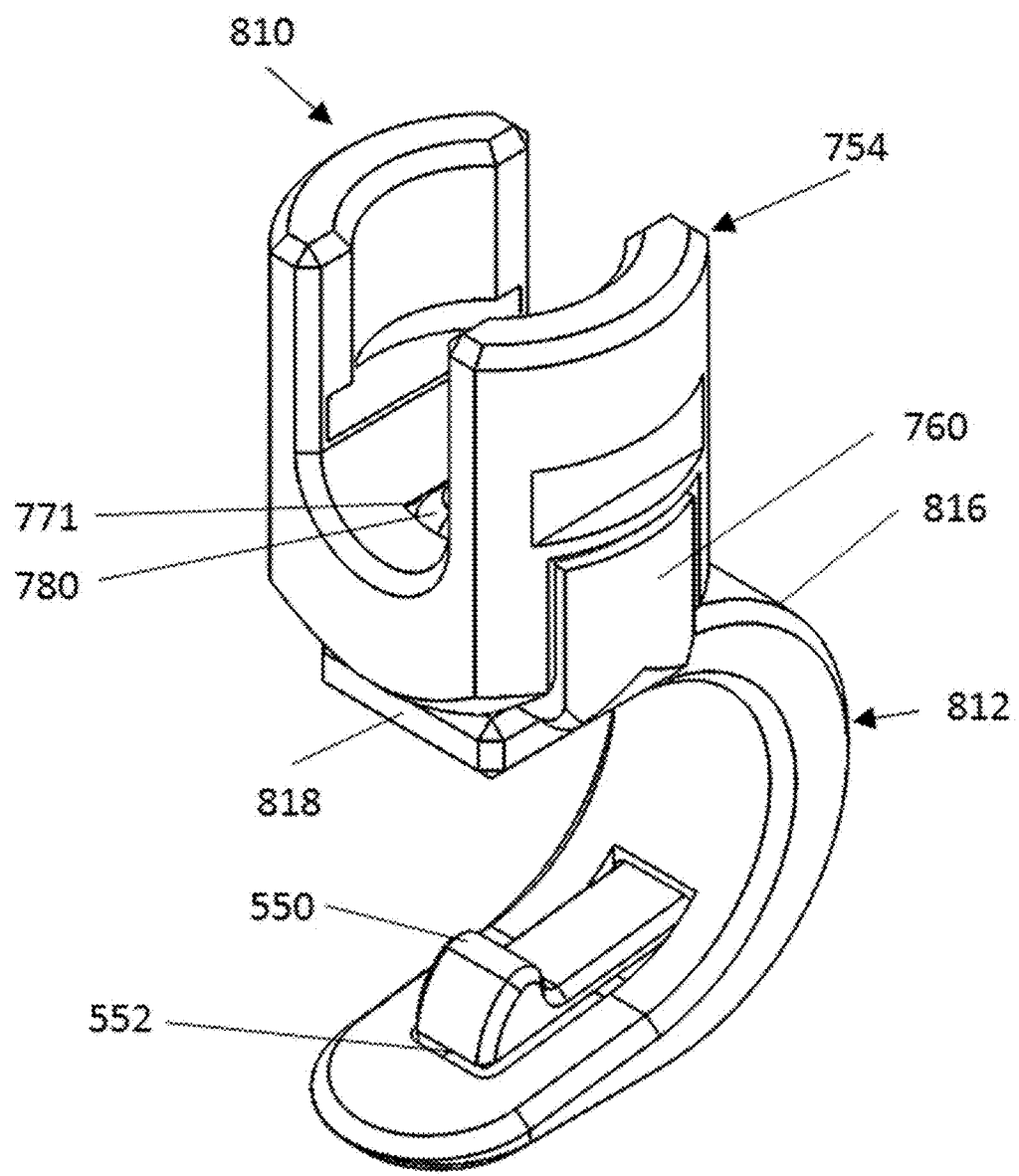
FIG. 23 is a perspective view of the eleventh embodiment of the spinal fixation device illustrated in FIG. 22.

An eleventh embodiment of a spinal fixation device is shown at 810 in FIGS. 22 and 23. The illustrated spinal fixation device 810 is substantially similar to the spinal fixation device 750. The spinal fixation device 810 includes the upper portion 754, the mounting bracket 760, and an alternate embodiment of the shoe portion 812. The mounting post 780, shown in FIG. 23, extends outwardly of an outside surface 816 of the first leg 818 of the shoe portion 812. The mounting post 780 is attached to the upper portion 754 as described above. Thus, the upper portion 754 and the shoe portion 812 of the spinal fixation device 810 are connected for translational or sliding movement relative to each other.

The shoe portion 812 is similar to the shoe portion 515 shown in FIGS. 13 and 14 and includes a bone facing surface 814 having the elongated groove 532 formed therein. The spring member 550, described in detail above, is attached within the groove 532 in the shoe portion 812.

Figure 24:
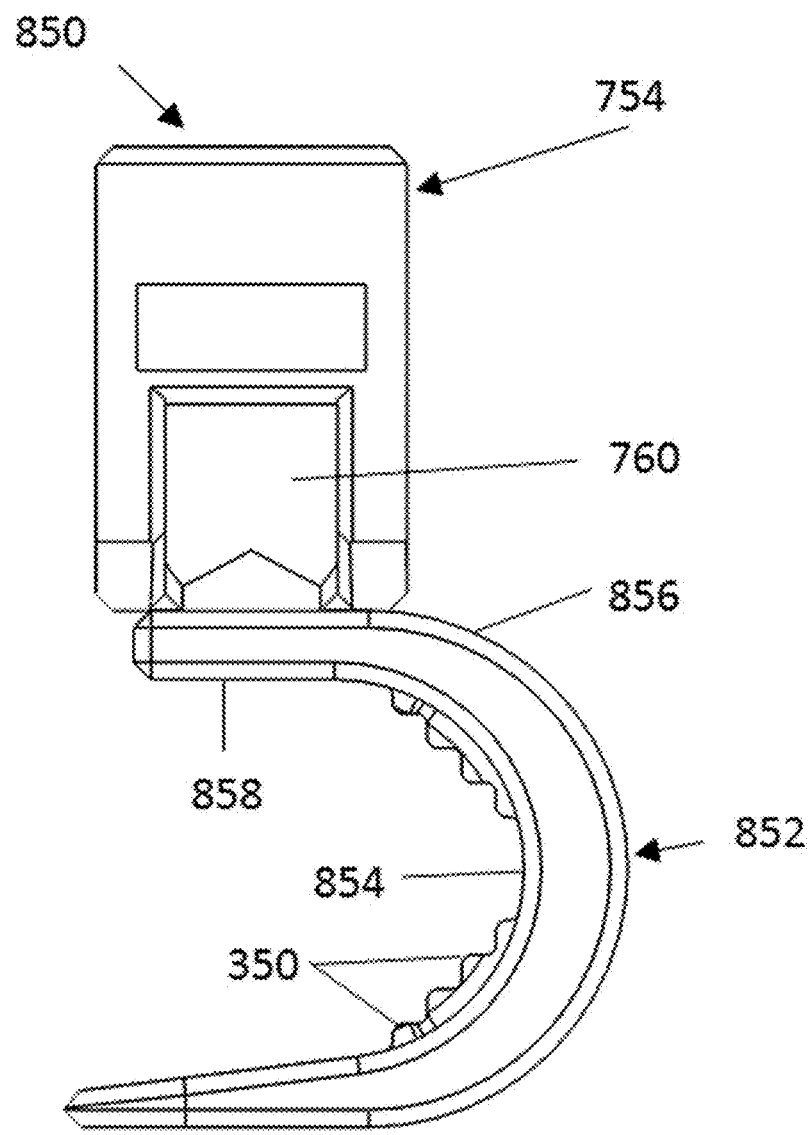
FIG. 24 is a side elevational view of a twelfth embodiment of a spinal fixation device in accordance with this invention.
Figure 25:
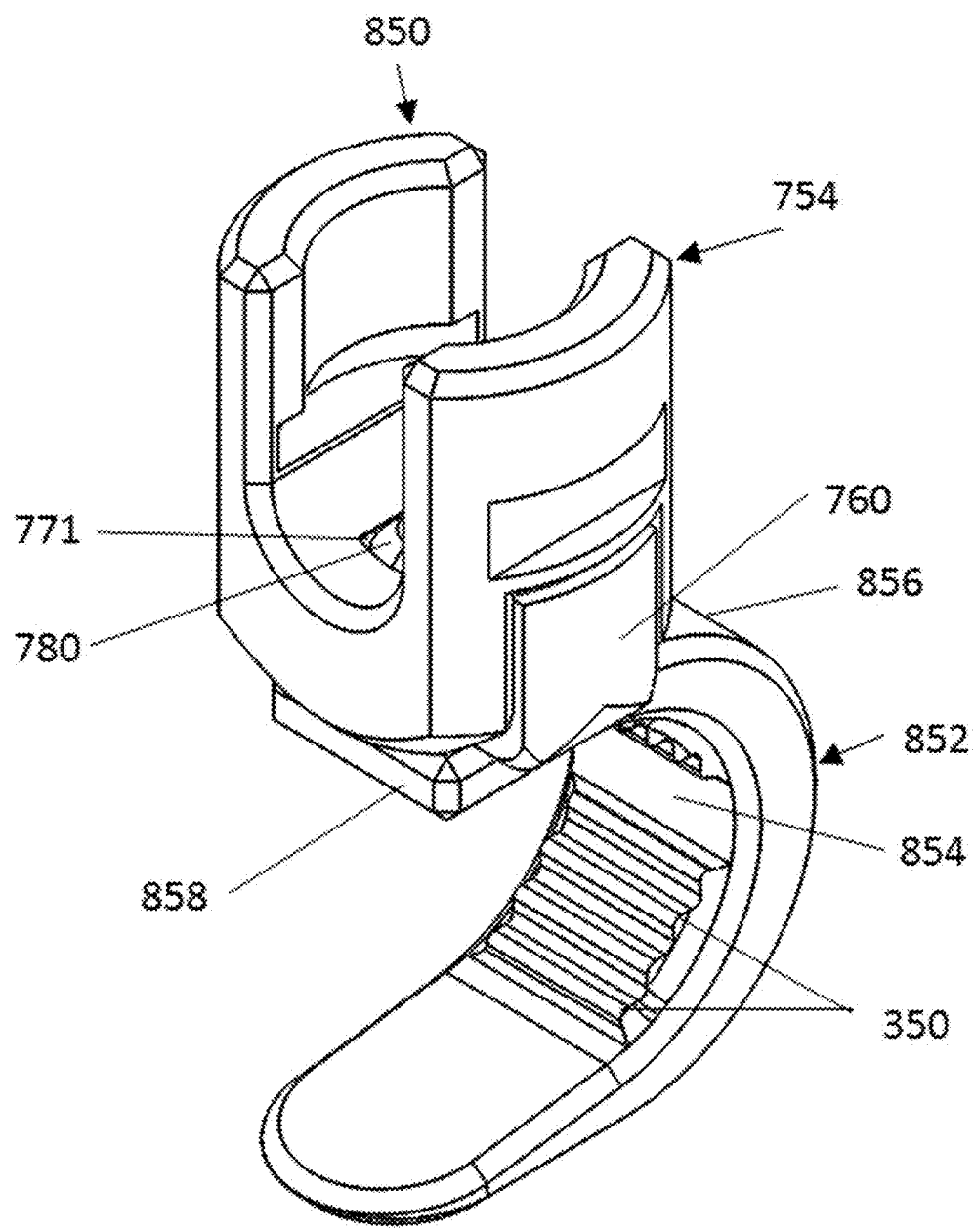
FIG. 25 is a perspective view of the twelfth embodiment of the spinal fixation device illustrated in FIG. 24.
Figure 26:
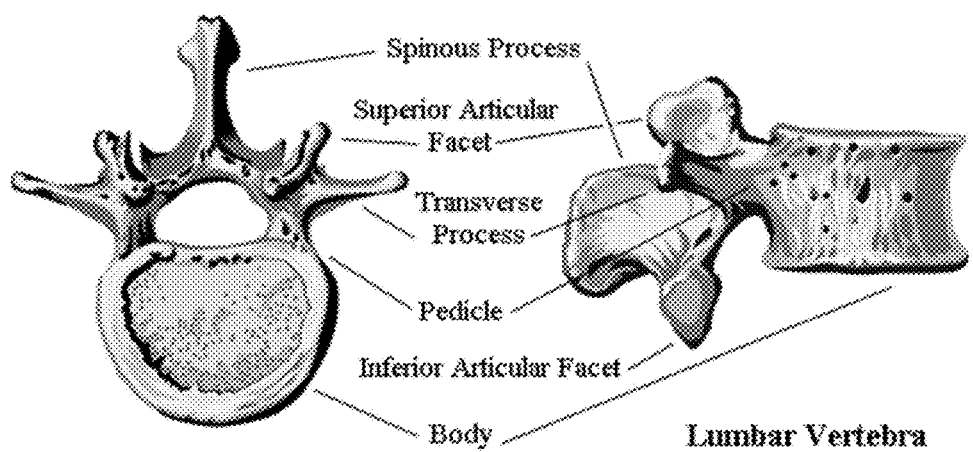
FIG. 26 is a top plan view of a representative human lumbar vertebra.
Figure 27:
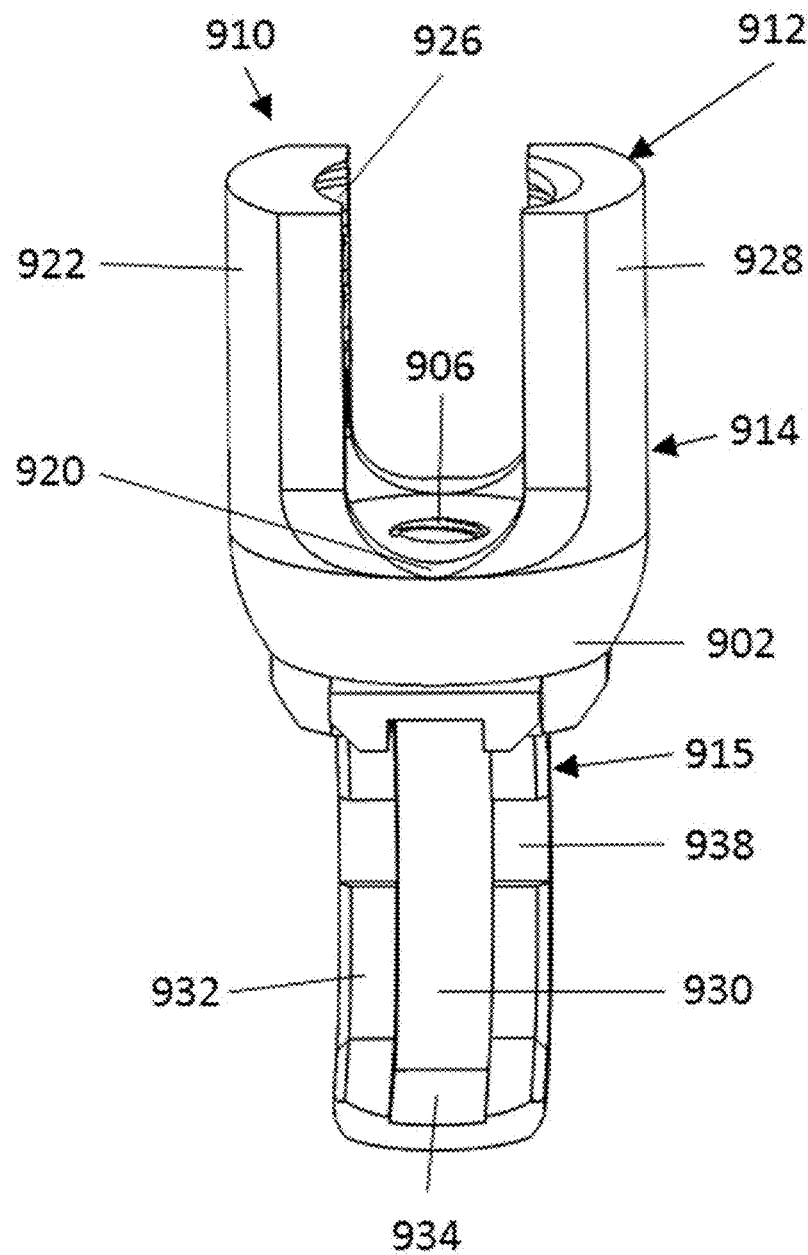
FIG. 27 is a perspective view of a thirteenth embodiment of a spinal fixation device in accordance with this invention.

A twelfth embodiment of a spinal fixation device is shown at 850 in FIGS. 24 and 25. The illustrated spinal fixation device 850 is substantially similar to the spinal fixation device 810 and includes the upper portion 754, the mounting bracket 760, and an alternate embodiment of the shoe portion 852. The mounting post 780, shown in FIG. 25, extends outwardly of an outside surface 856 of the first leg 858 of the shoe portion 852. The mounting post 780 is attached to the upper portion 754 as described above. Thus, the upper portion 754 and the shoe portion 852 of the spinal fixation device 850 are connected for translational or sliding movement relative to each other.

The shoe portion 852 is similar to the shoe portion 315 shown in FIG. 10 and includes a bone facing surface 854. A plurality of teeth 350, described in detail above, extend radially outward of the surface 854.

A thirteenth embodiment of a spinal fixation device is shown at 910 in FIGS. 27 through 30. The illustrated spinal fixation device 910 is similar to the spinal fixation device 10 and includes a hook base 912 having a first or tulip portion 914 and a shoe portion 915. The tulip portion 914 includes a semi-cylindrical lower portion 902, a channel 920 configured to receive the fusion rod 19, and two outwardly extending side walls 922. Interior surfaces 924 of the side walls 922 include threads 926. In the illustrated embodiment, outside surfaces 928 of the side walls 922 are arcuate, however the outside surfaces 928 may have any other desired shape. A threaded clamp bore 906 is formed through the lower portion 902 of the tulip portion 914 and the groove 934 of the shoe portion, described in detail below.

The shoe portion 915 extends outwardly from the tulip portion 914 opposite the side walls 922 and includes a bone facing surface 930. In the illustrated embodiment, the shoe portion 915 has an arcuate shape configured for attachment to various locations on the vertebrae, such as on the lamina, transverse process, or pedicle. The illustrated bone facing surface 930 also includes longitudinally extending ribs 932 defining a groove 934. Alternatively, the bone facing surface 930 may have any desired number of ribs 932 or may be formed without ribs, such as shown in the embodiments illustrated in FIGS. 6 through 25. The shoe portion 915 and its bone facing surface 930 may be formed in any desired shape so as to engage and facilitate attachment to various locations on the vertebrae. Fastener receiving notches 938 are formed in the grooves 934, and are configured to receive an attachment member 918, best shown in FIGS. 29 and 30. The illustrated attachment member 918 is a rectangular prism. Alternatively, the attachment member 918 may have any desired shape suitable for a press fit engagement with the shoe portion 915.

Figure 29:
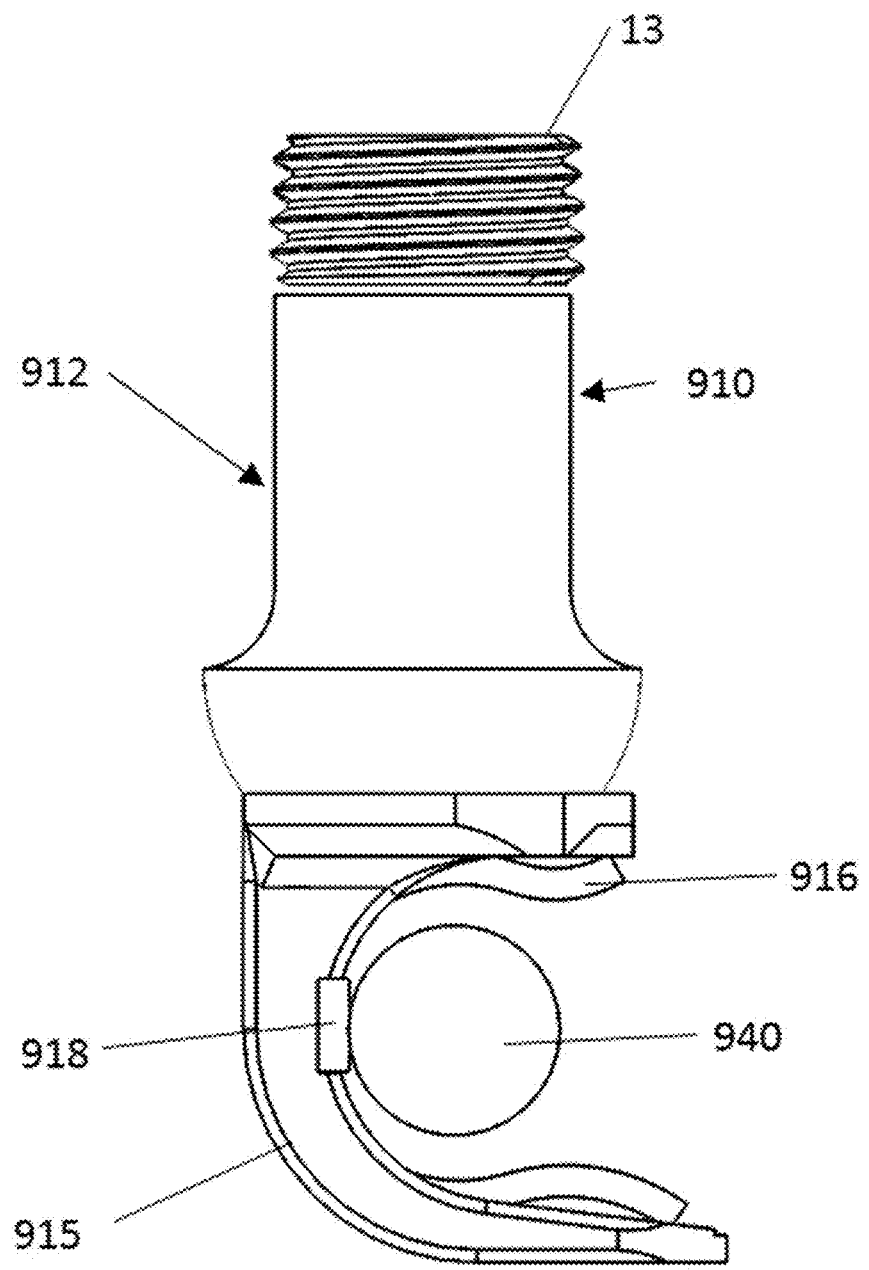
FIG. 29 is a side elevational view of the thirteenth embodiment of the spinal fixation device illustrated in FIG. 27, wherein the clamp is shown in an open position.
Figure 30:
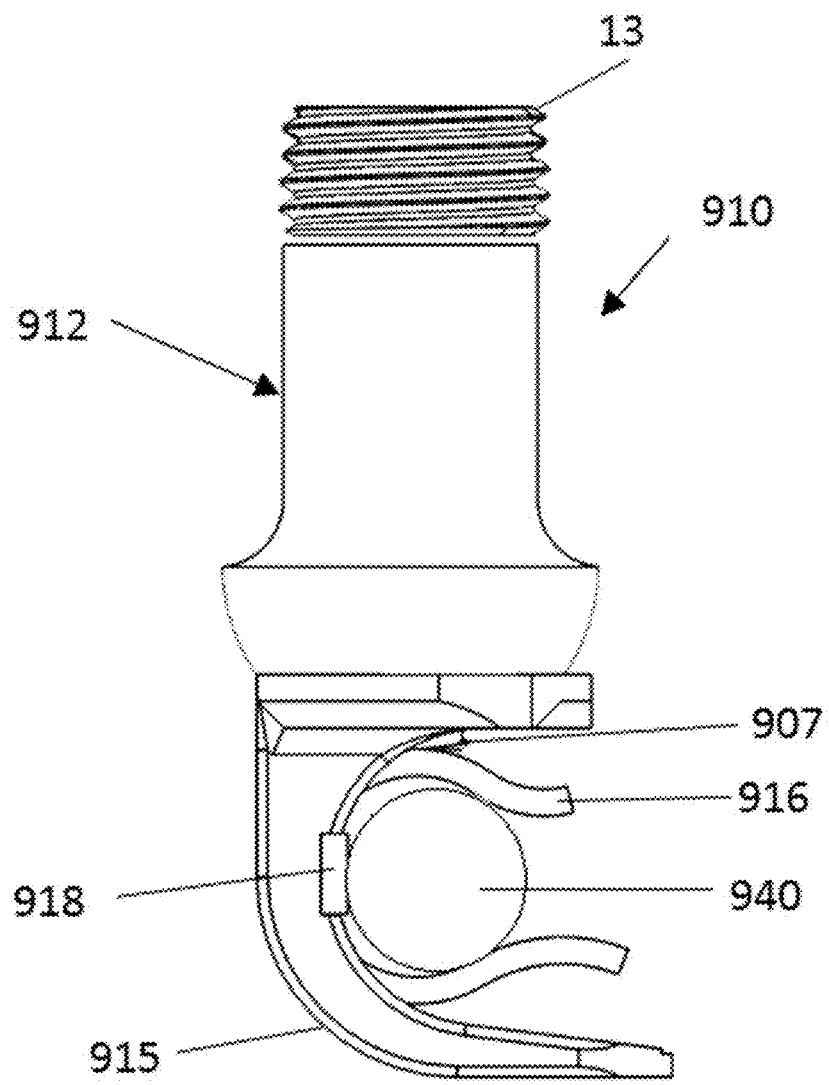
FIG. 30 is a side elevational view of the thirteenth embodiment of the spinal fixation device illustrated in FIG. 27, wherein the clamp is shown in a closed position.

The spinal fixation device 910 includes a clamp 916, as shown in FIGS. 29 and 30. The clamp 916 is similar to the clamp 16, but does not include a fastener receiving aperture. Like the clamp 16, the clamp 916 may be formed from shape memory material as described in detail above.

In the illustrated embodiment, the clamp 916 is positioned in the groove 934 and the attachment member 918 is press-fit into the notches 938, thus securely attaching the clamp 916 to the shoe portion 915. Alternatively, the clamp 916 may be attached to the shoe portion 915 by any desired means, such as the fastener 18 described above.

Referring again to FIGS. 29 and 30, an object 940 is shown within the clamp 916 and is representative of a portion of a vertebra to which the spinal fixation device 910 may be attached. In FIG. 29, the clamp 916 is shown in the open position, upon initial implantation in a patient's body. In FIG. 30, the clamp 916 is shown in the closed position, such as after the clamp 916 has been inside a patient's body for a period of time long enough for the temperature of the clamp 916 to rise to the temperature of the patient's body, i.e., at or about 37 degrees C. Once the clamp 916 transitions to the closed position, the spinal fixation device 910 may then be attached to a fusion rod 19 as described above.

Figure 28:
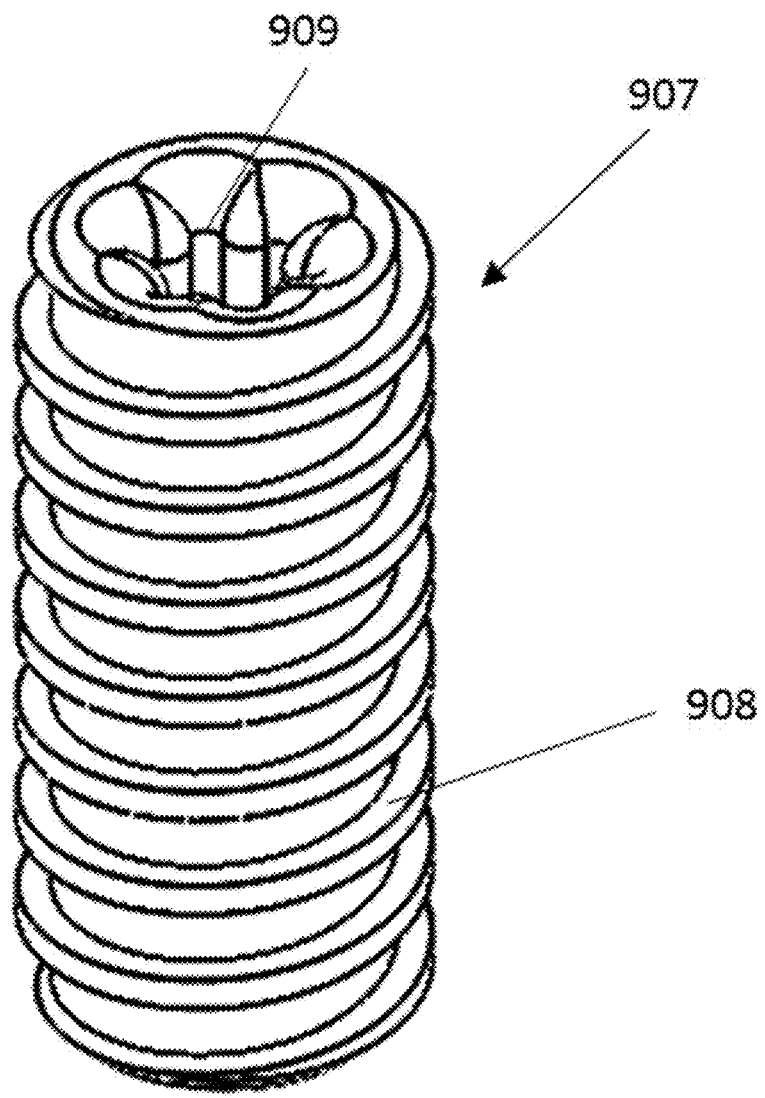
FIG. 28 is a perspective view of a first embodiment of a clamp screw for use in the spinal fixation device illustrated in FIG. 27.

Referring to FIG. 28, a clamp screw 907 is shown. The exemplary clamp screw 907 includes external threads 908 and a tool-receiving aperture 909. Optionally, once the clamp 916 transitions to the closed position, the surgeon may insert the clamp screw 907 into the clamp bore 906 and tighten the clamp screw 907 to further urge the clamp 916 against a vertebra, represented by object 940. The spinal fixation device 910 may then be attached to a fusion rod 19 as described above.

Figure 31:
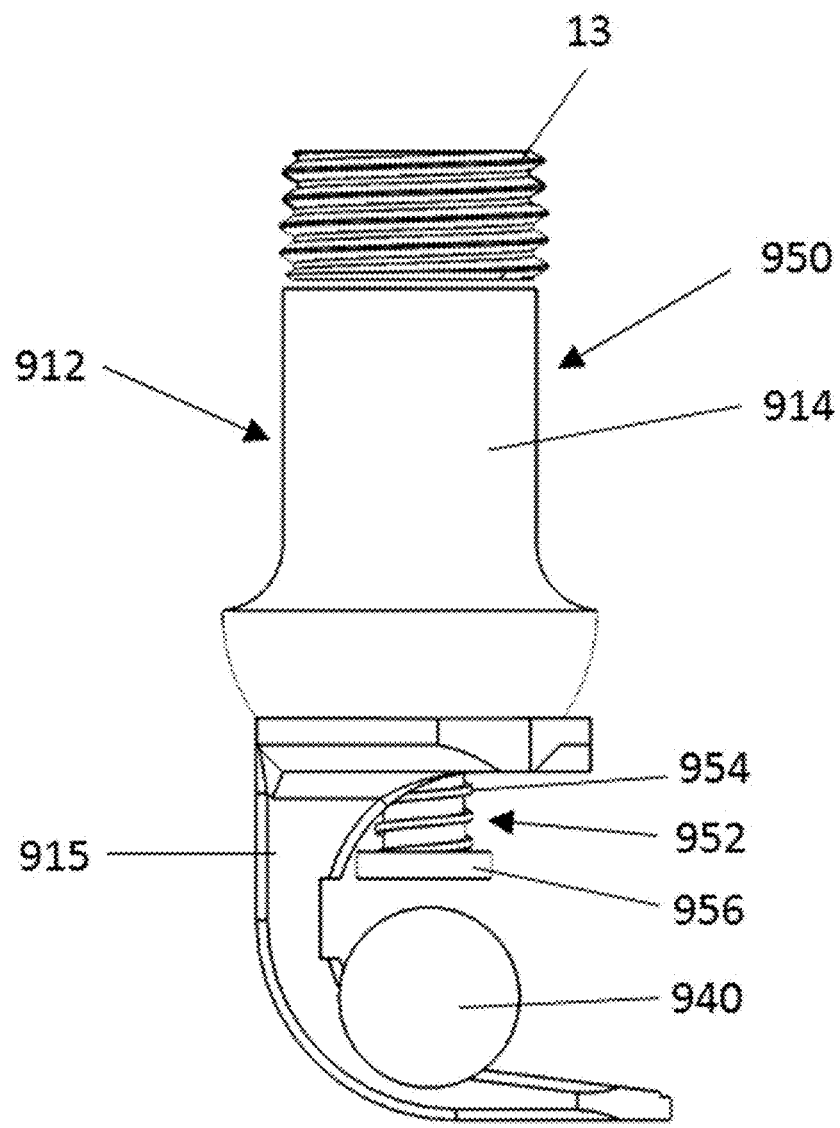
FIG. 31 is a side elevational view of a fourteenth embodiment of a spinal fixation device in accordance with this invention.

A fourteenth embodiment of a spinal fixation device is shown at 950 in FIG. 31. The illustrated spinal fixation device 950 is similar to the spinal fixation device 910 and includes the hook base 912, and shoe portion 915; a clamp, such as the clamp 916 is not required. The spinal fixation device 950 also includes a second embodiment of the clamp screw 952, shown extending outwardly of the clamp bore 906. The exemplary clamp screw 952 includes external threads 954 and the tool-receiving aperture 909, not shown in FIG. 31. The clamp screw 952 also includes a base plate 956.

In FIG. 31, the object 940 is shown within the shoe portion 915 and the spinal fixation device 950 is shown in a secured or closed position. As shown, the clamp screw 952 has been tightened until the base plate 956 engages a vertebra, represented by the object 940, and urges the vertebra against the bone facing surface 930 of the shoe portion 915, thus securing the spinal fixation device 950 to the vertebra. The spinal fixation device 950 may then be attached to a fusion rod 19 as described above.

Figure 31A:
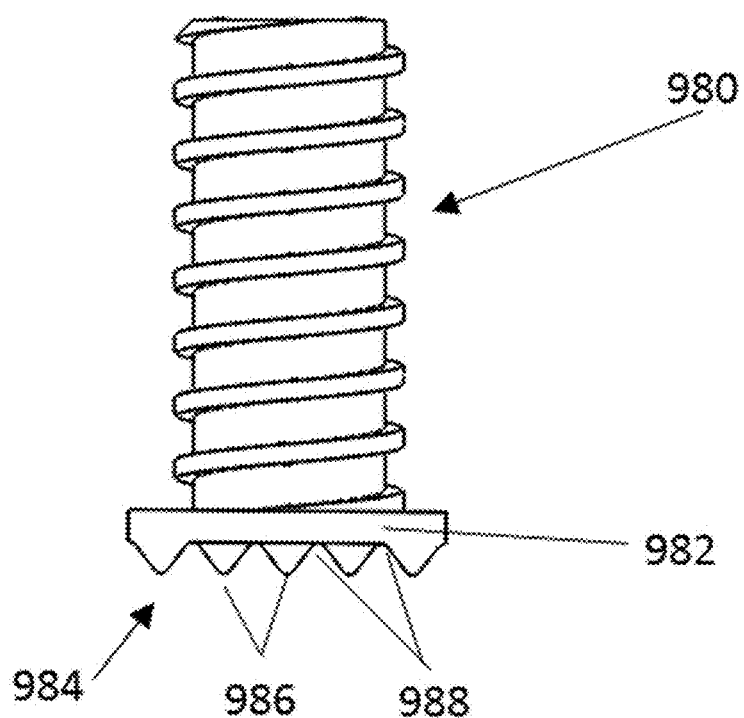
FIG. 31A is a side elevational view of a portion of a third embodiment of the clamp screw illustrated in FIG. 31.

A third embodiment of the clamp screw is shown at 980 in FIG. 31A. The clamp screw 980 includes a base plate 982 having a bone engaging surface 984. In the illustrated embodiment, the bone engaging surface 984 includes a plurality of parallel ridges 986 and grooves 988. Alternatively, the bone engaging surface 984 may have a knurled surface.

Figure 31B:
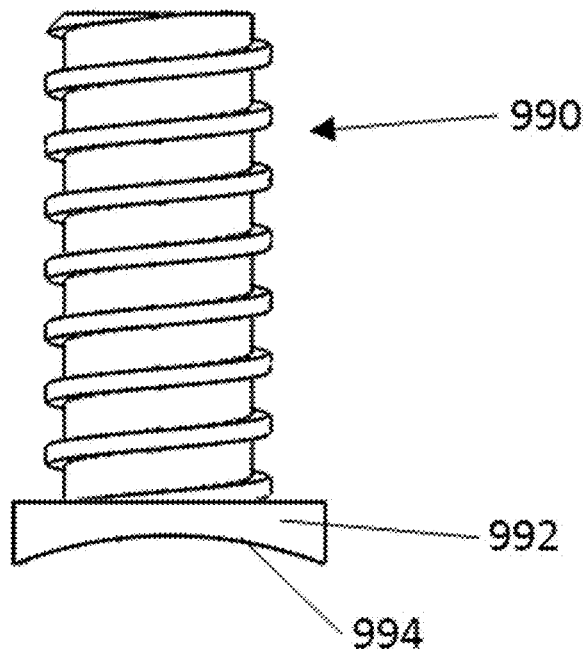
FIG. 31B is a side elevational view of a portion of a fourth embodiment of the clamp screw illustrated in FIG. 31.

A fourth embodiment of the clamp screw is shown at 990 in FIG. 31B. The clamp screw 990 includes a base plate 992 having a bone engaging surface 994. In the illustrated embodiment, the bone engaging surface 994 concave.

Figure 31C:
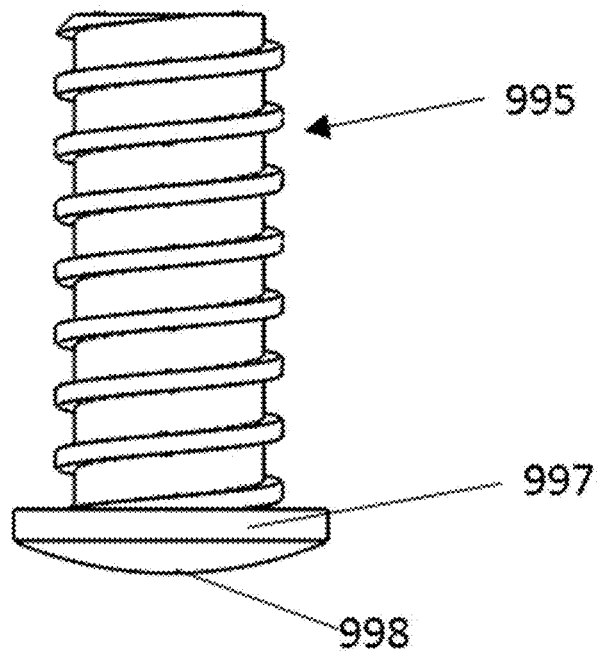
FIG. 31C is a side elevational view of a portion of a fifth embodiment of the clamp screw illustrated in FIG. 31.

A fifth embodiment of the clamp screw is shown at 995 in FIG. 31C. The clamp screw 995 includes a base plate 997 having a bone engaging surface 998. In the illustrated embodiment, the bone engaging surface 998 is convex.

It will be understood that any embodiment of the shoe portion described herein may be formed from any of the shape memory materials also described herein.

Figure 32:
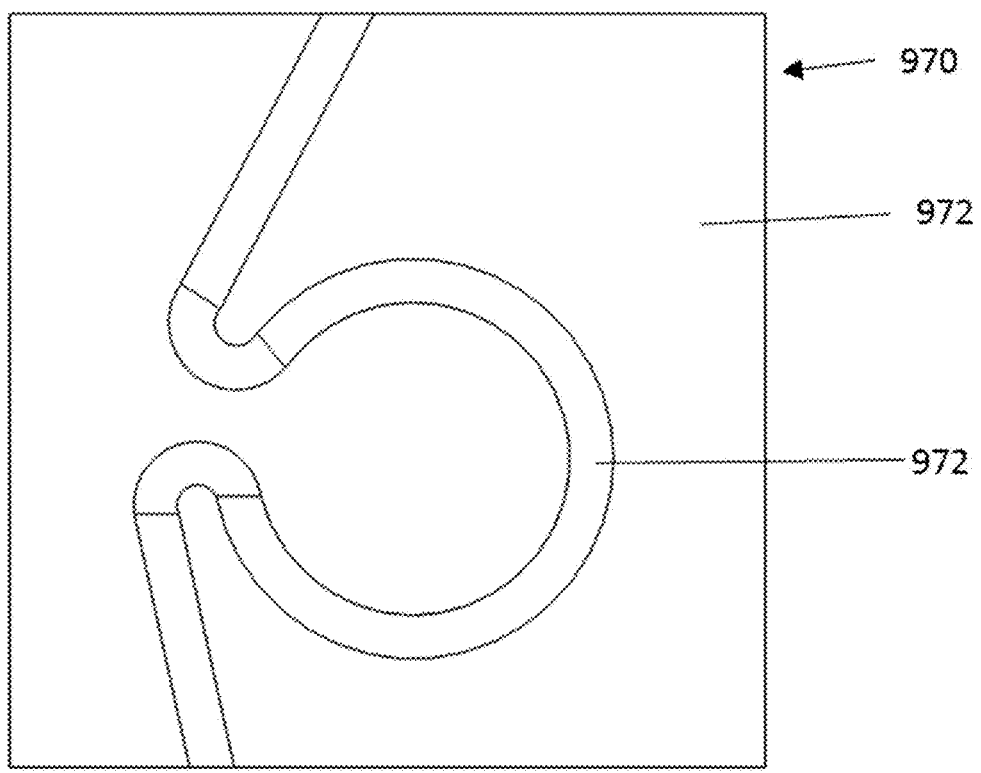
FIG. 32 is a perspective view of a first embodiment of a mold used to form the clamps illustrated in FIGS. 1 through 5, 29 and 30.

FIG. 32 illustrates an exemplary mold 970 for forming a shape memory clamp, such as the clamps 16 and 916 described above. The mold 970 has a mold surface 972. A cavity 974 is formed in the mold surface. In the embodiment of the mold 970 shown in FIG. 32, the mold cavity 974 has the desired shape of a clamp when the clamp is in the closed position as shown in FIGS. 2, 3, and 30; i.e. the shape the clamp assumes when its temperature rises to the temperature of a patient's body, that is at or about 37 degrees C.

In operation, a strip of shape memory material, such as nitinol is placed in the mold cavity 974. The mold 970 is then placed in an oven and heated to a temperature of about 500 degrees C., thereby setting the hot temperature shape, or the shape the clamp assumes upon reaching a temperature at or about 37 degrees C.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A spinal fixation device comprising:
a device body configured for implantation in a human body and including a hook base having an upper portion and an arcuate shoe portion comprising a first leg adjacent to the hook base, the first leg defining an outside surface and a bone facing surface, wherein a channel is formed in the outside surface;
a clamp formed from shape memory material and attached to the device body;
a mounting post extending outward from the outside surface between a distal end of the first leg and the channel, wherein the mounting post is formed in quarters defined by longitudinally extending channels intersecting to define a pin bore; and
a mounting bracket having a base and two outwardly extending side walls, wherein a translational slot is formed through the base;
wherein the two side walls of the mounting bracket fit within the channel, and the mounting post extends through the translational slot of the mounting bracket so as to allow for translational or sliding movement of the upper portion relative to the shoe portion.

2. The spinal fixation device according to claim 1, wherein the clamp is formed in a closed position and configured to be positioned one of against and at least partially around a portion of a vertebra.

3. The spinal fixation device according to claim 2, wherein the clamp responds to changes in temperature such that when the clamp is deformed or enlarged when positioned against or at least partially around a portion of a vertebra, upon reaching human body temperature or about 37 degrees, the clamp will attempt to return to its closed shape, thereby exerting a clamping force on the portion of the vertebra.

4. The spinal fixation device according to claim 3, wherein the clamp is an elongated member having a bone engaging surface.

5. The spinal fixation device according to claim 4, wherein the elongated member has an arcuate shape.

6. The spinal fixation device according to claim 4, wherein the elongated member is mounted to the device body in a cantilevered manner.

7. The spinal fixation device according to claim 1, wherein the clamp is attached to the device body by a fastener.

8. The spinal fixation device according to claim 7, wherein the fastener is a rivet.

9. The spinal fixation device according to claim 7, wherein the fastener is a threaded fastener.

10. The spinal fixation device according to claim 7, wherein the fastener is configured to be press fit to the device body.

11. The spinal fixation device according to claim 7, wherein the clamp is integrally formed with the device body.

12. The spinal fixation device according to claim 1, wherein the clamp responds to changes in temperature such that at a first temperature, the clamp is in an open position, and at a second temperature, higher than the first temperature, the clamp is in a closed position.

13. The spinal fixation device according to claim 12, wherein in the open position the clamp is configured to be positioned one of against and at least partially around a portion of a vertebra; and
wherein in the closed position the clamp exerts a clamping force on the portion of the vertebra, thereby attaching the spinal fixation device to the vertebra.

14. The spinal fixation device according to claim 12, wherein the first temperature is room temperature or about 21 degrees C., and the second temperature is human body temperature or about 37 degrees C.

15. The spinal fixation device according to claim 1, wherein the clamp is movable between an open position and a closed position.

16. The spinal fixation device according to claim 15, wherein in the open position the clamp is configured to be positioned one of against and at least partially around a portion of a vertebra; and
wherein in the closed position the clamp exerts a clamping force on the portion of the vertebra, thereby attaching the spinal fixation device to the vertebra.

17. The spinal fixation device according to claim 1, wherein the shoe portion is formed from shape memory material.

18. The spinal fixation device according to claim 1, wherein the clamp is an elongated member having a bone engaging surface and is configured to exert a clamping force on a portion of a vertebra positioned between the clamp and the shoe portion.

19. The spinal fixation device according to claim 1, wherein upon insertion of a locking pin into the pin bore, the locking pin urges an outside surface of the base to frictionally engage an inside surface of the shoe portion, preventing movement of the base relative to the shoe portion.

20. The spinal fixation device according to claim 1, wherein the hook base and the shoe portion are connected by a joint that allows translational movement between the hook base and the shoe portion.

* * * * *